US010080773B2

(12) United States Patent
Cogan et al.

(10) Patent No.: US 10,080,773 B2
(45) Date of Patent: Sep. 25, 2018

(54) PROBIOTIC FORMULATION

(75) Inventors: Tristan Cogan, Bristol (GB); Jenny Bailey, Bristol (GB)

(73) Assignee: The University of Bristol, Bristol (GB)

( * ) Notice: Subject to any disclaimer, the term of this patent is extended or adjusted under 35 U.S.C. 154(b) by 69 days.

(21) Appl. No.: 14/232,852

(22) PCT Filed: Jul. 19, 2012

(86) PCT No.: PCT/GB2012/051730
§ 371 (c)(1),
(2), (4) Date: Apr. 23, 2014

(87) PCT Pub. No.: WO2013/011320
PCT Pub. Date: Jan. 24, 2013

(65) Prior Publication Data
US 2015/0098929 A1   Apr. 9, 2015

(30) Foreign Application Priority Data

Jul. 21, 2011  (GB) .................................. 1112487.2

(51) Int. Cl.
*A61K 9/12* (2006.01)
*A61K 35/744* (2015.01)
*A23C 9/123* (2006.01)
*C12R 1/44* (2006.01)
*C12N 1/20* (2006.01)
*A23L 2/52* (2006.01)
*A23C 9/12* (2006.01)
*C12R 1/46* (2006.01)
*A23L 33/135* (2016.01)

(52) U.S. Cl.
CPC .............. *A61K 35/744* (2013.01); *A23C 9/12* (2013.01); *A23C 9/1238* (2013.01); *A23L 2/52* (2013.01); *A23L 33/135* (2016.08); *C12N 1/20* (2013.01); *C12R 1/44* (2013.01); *C12R 1/46* (2013.01); *A23V 2002/00* (2013.01); *A23Y 2240/75* (2013.01)

(58) Field of Classification Search
None
See application file for complete search history.

(56) References Cited

U.S. PATENT DOCUMENTS

2009/0110663 A1   4/2009  Halow

FOREIGN PATENT DOCUMENTS

EP           1481681 A1    12/2004
WO      WO 2011/050426 A2    5/2011

OTHER PUBLICATIONS

SCORE search results conducted on Sep. 16, 2015.*
Sheil et al., The Journal of Nutrition, 2007, vol. 137, 819S-824S.*
Herve-Jimenez, L., et al., "Postgenomic Analysis of *Streptococcus thermophilus* Cocultivated in Milk with *Lactobacillus delbrueckii* subsp. *bulgaricus*: Involvement of Nitrogen, Purine, and Iron Metabolism", Applied and Environmental Microbiology, vol. 75, No. 7, pp. 2062-2073 (2009).
Sieuwerts, S., et al., "Mixed-Culture Transcriptome Analysis Reveals the Molecular Basis of Mixed-Culture Growth in *Streptococcus thermophilus* and *Lactobacillus bulgaricus*", Applied and Environmental Microbiology, vol. 76, No. 23, pp. 7775-7784 (2010).
Simova, E. et al., "Growth and activity of Bulgarian yogurt starter culture in iron-fortified milk", Journal of Industrial Microbiology & Biotechnology, vol. 35, No. 10, pp. 110-1115 (2008).
Bailey, et al., "Identification and characterisation of an iron-responsive candidate probiotic", PLoS One, 2011;6(10): e26507, pp. 1-10.
Anukam et al., "Yogurt Containing Probiotic Lactobacillus rhamnosus GR-1 and L. reuteri RC-14 Helps Resolve Moderate Diarrhea and Increases CD4 Count in HIV/AIDS Patients," Journal of Clinical Gastroenterology, 2008, pp. 239-243, vol. 42, No. 3.
Archibald, "Manganese; Its Acquisition by and Function in the Lactic Acid Bacteria," CRC Critical Reviews in Microbiology, 1986, pp. 63-109, vol. 13, No. 1.
Bibiloni et al., "VSL#3 Probiotic-Mixture Induces Remission in Patients with Active Ulcerative Colitis," American Journal of Gastroenterology, 2005, pp. 1539-1546, vol. 100.
Botina et al., "Genetic Diversity of the Natural Strains of Streptococcus thermophilus," Russian Journal of Genetics, 2007, pp. 485-491, vol. 43, No. 5.
Bruyneel et al., "Lactic Acid Bacteria: Micro-Organisms Able to Grow in the Absence of Available Iron and Copper," Biotechnology Letters, 1989, pp. 401-406, vol. 11, No. 6.
de Chambrun et al., "Pathogenic agents in inflammatory bowel diseases," Current Opinion in Gastroenterology, 2008, 440-447, vol. 24.
Freestone et al., "Stimulation of bacterial growth by heat-stable, norepinephrine-induced autoinducers," FEMS Microbiology Letters, 1999, pp. 53-60, vol. 172.
Freestone et al., "Growth Stimulation of Intestinal Commensal Escherichia Coli by Catecholamines: A Possible Contributory Factor in Trauma-Induced Sepsis," Shock, 2002, pp. 465-470, vol. 18, No. 5.
Furet et al., "Molecular quantification of lactic acid bacteria in fermented milk products using real-time quantitative PCR," International Journal of Food Microbiology, 2004, pp. 197-207, vol. 97.
Gronbach et al., "Safety of Probiotic Escherichia coli Strain Nissle 1917 Depends on Intestinal Microbiota and Adaptive Immunity of the Host," Infection and Immunity, 2010, pp. 3036-3046, vol. 78, No. 7.
Hafez et al., "The K5 Capsule of Escherichia coli Strain Nissle 1917 Is Important in Stimulating Expression of Toll-Like Receptor 5, CD14, MyD88, and TRIF Together with the Induction of Interleukin-8 Expression via the Mitogen-Activated Protein Kinase Pathway in Epithelial Cells," Infection and Immunity, 2010, pp. 2153-2162, vol. 78, No. 5.

(Continued)

*Primary Examiner* — Kade Ariani

(57) ABSTRACT

A probiotic organism which is capable of proliferation in iron-rich media, an environment which is generally unfavorable to probiotic organisms, is described.

11 Claims, 26 Drawing Sheets

Specification includes a Sequence Listing.

(56) References Cited

OTHER PUBLICATIONS

Haller et al., "Guidance for Substantiating the Evidence for Beneficial Effects of Probiotics: Probiotics in Chronic Inflammatory Bowel Disease and the Functional Disorder Irritable Bowel Syndrome," The Journal of Nutrition, 2010, pp. 690S-697S, vol. 140.

Hickson et al., "Use of probiotic Lactobacillus preparation to prevent diarrhoea associated with antibiotics: randomised double blind placebo controlled trial," BMJ, 2007, 5 pgs., vol. 335.

Hoffmann et al., "Lactobacillus reuteri 100-23 Transiently Activates Intestinal Epithelial Cells of Mice That Have a Complex Microbiota during Early Stages of Colonization," The Journal of Nutrition, 2008, pp. 1684-1691, vol. 138.

Imbert et al., "On the Iron Requirement of Lactobacilli Grown in Chemically Defined Medium," Current Microbiology, 1998, pp. 64-66, vol. 37.

Inman et al., "Validation of computer-assisted, pixel-based analysis of multiple-colour immunofluorescence histology," Journal of Immunological Methods, 2005, pp. 156-167, vol. 302.

Kwon et al., "Generation of regulatory dendritic cells and CD4+ Foxp3+ T cells by probiotics administration suppresses immune disorders," PNAS, 2010, pp. 2159-2164, vol. 107, No. 5.

McFarland, "Meta-analysis of probiotics for the prevention of traveler's diarrhea," Travel Medicine and Infectious Disease, 2007, pp. 97-105, vol. 5.

Pagnini et al., "Probiotics promote gut health through stimulation of epithelial innate immunity," PNAS, 2010, pp. 454-459, vol. 107, No. 1.

Pandey et al., "Iron requirement and search for siderophores in lactic acid bacteria," Applied Microbiology and Biotechnology, 1994, pp. 735-739, vol. 40.

Rembacken et al., "Non-pathogenic Escherichia coli versus mesalazine for the treatment of ulcerative colitis: a -andomised trial," The Lancet, 1999, pp. 635-639, vol. 354.

Report of a Joint FAO/WHO Expert Consultation on Evaluation of Health and Nutritional Properties of Probiotics in Food including Powder Milk with Live Lactic Acid Bacteria, Oct. 2001, Cordoba, Argentina; 34 pgs.

Rodriguez et al., "Therapeutic effect of Streptococcus thermophilus CRL 1190-fermented milk on chronic gastritis," World Journal of Gastroenterology, 2010, pp. 1622-1630, vol. 16, No. 13.

Roselli et al., "Prevention of TNBS-Induced Colitis by Different Lactobacillus and Bifidobacterium Strains Is Associated with an Expansion of γσT and Regulatory T Cells of Intestinal Intraepithelial Lymphocytes," Inflamm Bowel Dis, 2009, pp. 1526-1536, vol. 15, No. 10.

Sandrini et al., "Elucidation of the Mechanism by Which Catecholamine Stress Hormones Liberate Iron from the Innate Immune Defense Proteins Transferrin and Lactoferrin," Journal of Bacteriology, 2010, pp. 587-594, vol. 192, No. 2.

Singh et al., "CXCR3 Axis: Role in Inflammatory Bowel Disease and its Therapeutic Implication," Endocrine, Metabolic & Immune Disorders—Drug Targets, 2007, pp. 111-123, vol. 7.

Sokol et al., "Faecalibacterium prausnitzii is an anti-inflammatory commensal bacterium identified by gut microbiota analysis of Crohn disease patients," PNAS, 2008, pp. 16731-16736, vol. 105, No. 43.

Stallmach et al., "Activation of β1 integrins mediates proliferation and inhibits apoptosis of intestinal CD4-positive lymphocytes," European Journal of Immunology, 2001, pp. 1228-1238, vol. 31.

Sturm et al., "Dual Function of the Extracellular Matrix: Stimulatory for Cell Cycle Progression of Naive T Cells and Antiapoptotic for Tissue-Derived Memory T Cells," The Journal of Immunology, 2004, pp. 3889-3900, vol. 173.

Subramanian et al., "Characterization of Epithelial IL-8 Response to Inflammatory Bowel Disease Mucosal E. coli and Its Inhibition by Mesalamine," Inflamm Bowel Dis, 2008, pp. 162-175, vol. 14, No. 2.

Szajewska et al., "Meta-analysis: Lactobacillus GG for treating acute diarrhoea in children," Alimentary Pharmacology & Therapeutics, 2007, pp. 871-881, vol. 25.

Tursi et al., "Low-dose balsalazide plus a high-potency probiotic preparation is more effective than balsalazide alone or mesalazine in the treatment of acute mild-to-moderate ulcerative colitis," Med Sci Monit, 2004, pp. PI126-PI131, vol. 10, No. 11.

van Baarlen et al., "Differential NF-KN pathways induction by Lactobacillus plantarum in the duodenum of healthy humans correlating with immune tolerance," PNAS, 2009, pp. 2371-2376, vol. 106, No. 7.

Venturi et al., "Impact on the composition of the faecal flora by a new probiotic preparation: preliminary data on maintenance treatment of patients with ulcerative colitis," Aliment Pharmacol Ther, 1999, pp. 1103-1108, vol. 13.

Wooldridge et al., "Iron uptake mechanisms of pathogenic bacteria," FEMS Microbiology Reviews, 1993, pp. 325-348, vol. 12.

* cited by examiner

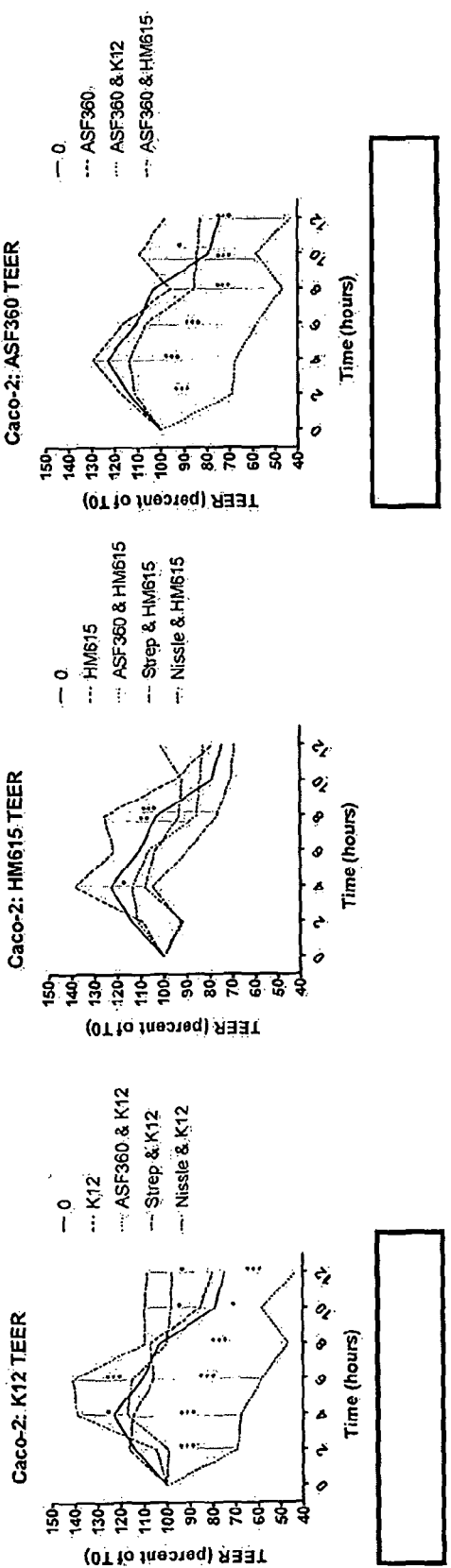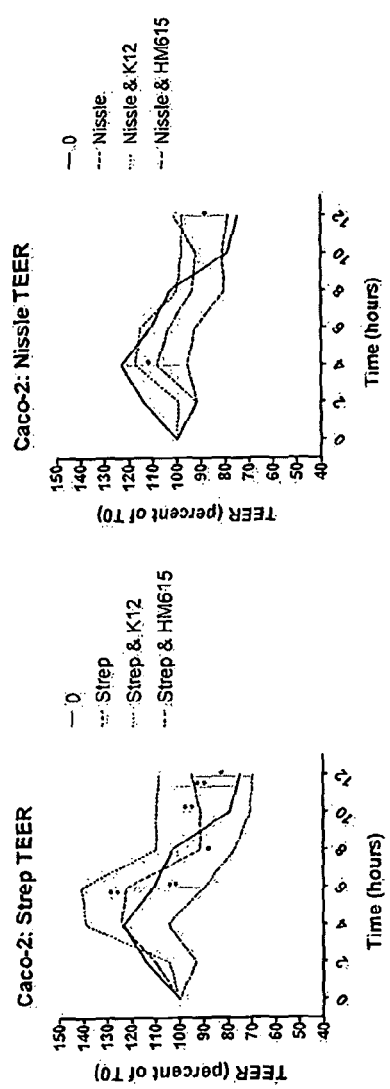
Figure 2

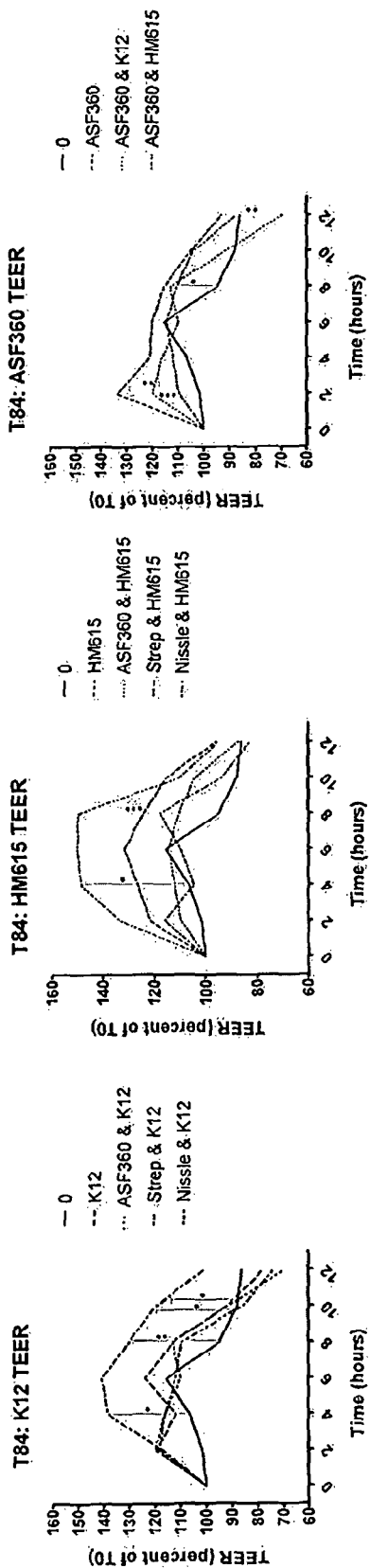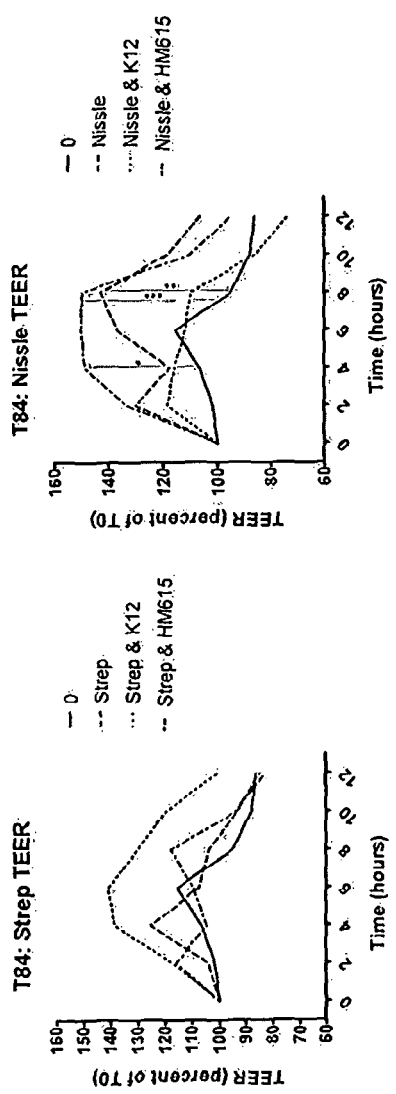
Figure 3

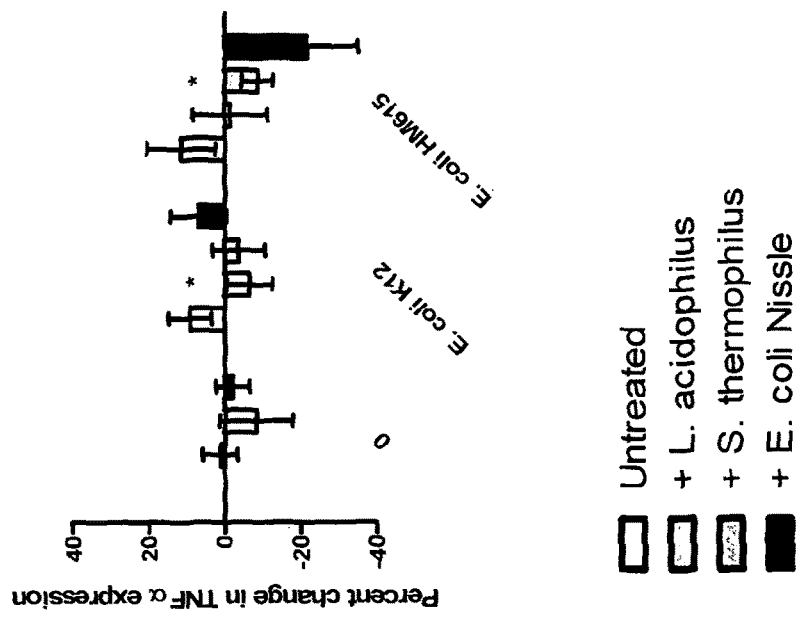
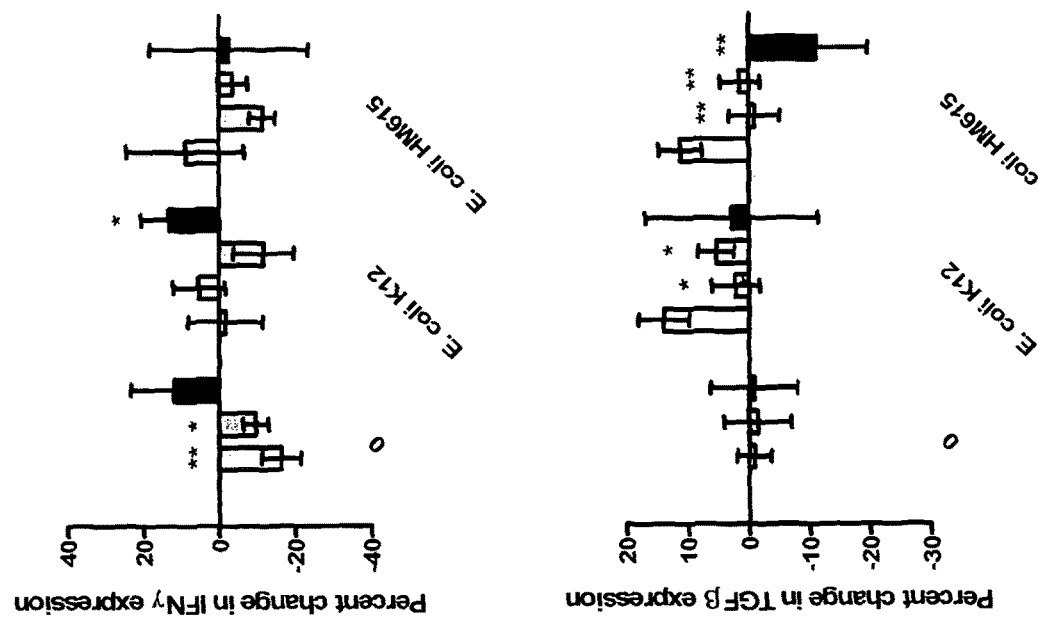
Figure 9

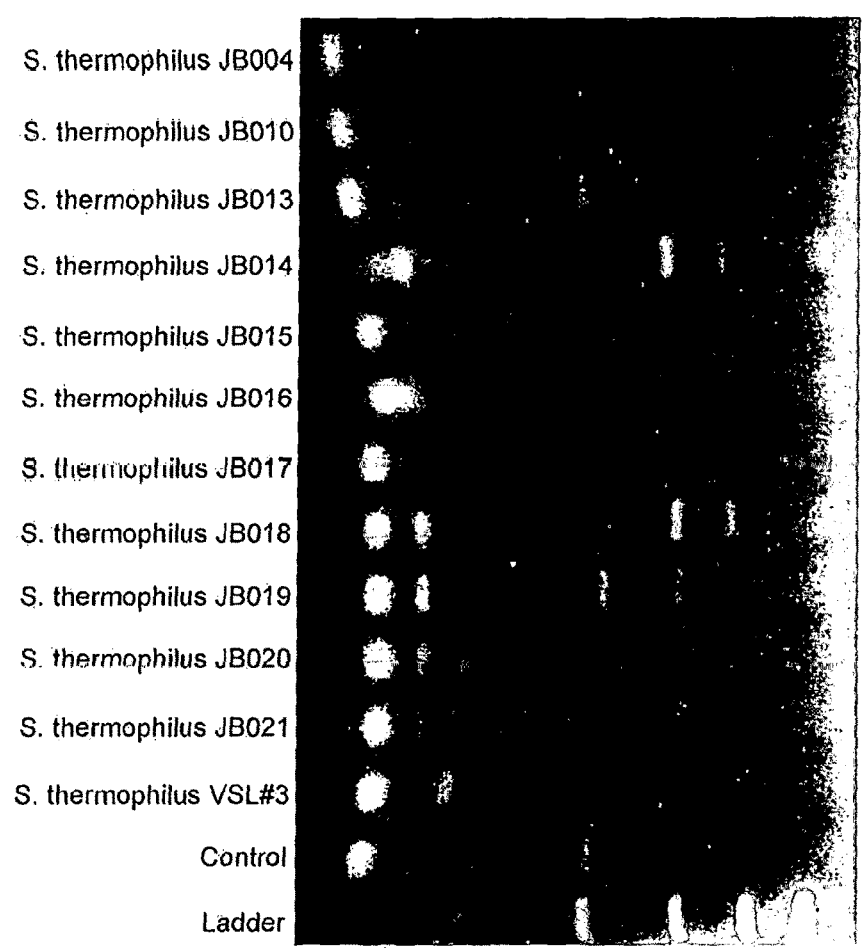
Figure 10    NB: S. thermophilus JB010 = NCIMB 41856

Figure 11 sodA

ATGGTAAGATGGAAAAAAATGAAAGAGGACCTTTACTATGGCTATTATTCTTCC
AGATCTTCCTTACGCTTACGATGCTTTGGAACCATACATTGATGCTGAAACAATG
ACTCTTCATCATGACAAACACCATGCAACTTACGTGGCGAATGCTAATGCTGCGC
TTGAAAAACACCCTGAAATTGGTGAGGACCTTGAAGCGCTTTTGGCTGATGTAGA
AAAAATTCCAGCAGACATCCGTCAAGCACTTATTAACAATGGTGGTGGACATCTT
AACCACGCACTTTTCTGGGAACTTTTGTCACCAGAAAAACAAGAACCAACTGCA
GAAGTAGCAGCTGCTATTAACGAAGCATTCGGTTCATTTGAAGCTTTCCAAGAAG
TTTTCACTACGGCAGCGACAACTCGTTTTGGTTCAGGGTGGGCATGGCTTGTGGT
TAACGCAGAAGGTAAACTTGAAGTTGTTTCAACTCCCAACCAAGATACACCTATC
TCAGACGGTAAAAAACCAATCTTGGCACTTGATGTTTGGGAACATGCTTACTACC
TAAAATACCGTAACGTACGTC dpr GACACCAACAAACACAAAAACCAAAGCAGTATTAAATCAAGCGGTTGCCGATTT
GTCTGTAGCAGCTTCTATTGTGCATCAAGTTCATTGGTATATGCGTGGTCCTGGTT
TCCTTTATCTTCACCCAAAAATGGATGAATTAATGGATAGTTTGAATTCCTATCTT
GATAAGATTAGTGAGCGTTTGATTACCATTGGTGGTGAACCCTACTCAACTTTGG
TAGAGTTTTCATCTAATTCAGGTTTGACTGAAACTACTGGTACATTTGATCAACC
AATGTCTGATCGAATTCAGCTATTGGTTGATATATACAAATACTTGTCTGTCTTGT
TCCAAGTTGGCTTGGATATTACAGATGAAGAAGGAGATGTTCCTTCAAATGATAT
CTTTACGGATGCAAAATCAGAAATTGATAAGACGATCTG rpoB CCTAAGGGTGAAAAAGACCTTTCTGCTGAAGAACGTCTTCTCCATGCTATCTTTG
GTGATAAATCTCGTGAAGTACGTGATACATCACTCCGTGTACCTCATGGTGGTGA
TGGTGTCGTTCGTGATGTTAAAATCTTTACACGTGCAAACGGTGATGAATTGCAA
TCAGGTGTTAACATGCTTGTTCGTGTTTACATCGCTCAAAAACGTAAAATCAAGG
TCGGAGATAAGATGGCTGGTCGTCACGGTAACAAAGGGGTTGTTTCTCGTATTGT
TCCTGTTGAAGACATGCCTTACCTTCCAGACGGTACACCAGTTGACATCATGTTG
AACCCTCTTGGGGTGCCATCACGTATGAACATTGGTCAGGTTATGGAACTTCACC
TTGGTATGGCTGCTCGTAACTTGGGTATCTACATCGCAACACCAGTCTT 16s AGAGTTTGATCCTGGCTCAGGACGAACGCTGGCGGCGTGCCTAATACATGCAAG
TAGAACGCTGAAGAGAGGAGCTTGCTCTTCTTGGATGAGTTGCGAACGGGTGAG
TAACGCGTAGGTAACCTGCCTTGTAGCGGGGGATAACTATTGGAAACGATAGCT
AATACCGCATAACAATGGATGACACATGTCATTTATTTGAAAGGGGCAATTGCTC
CACTACAAGATGGACCTGCGTTGTATTAGCTAGTAGGTGAGGTAATGGCTCACCT
AGGCGACGATACATAGCCGACCTGAGAGGGTGATCGGCCACACTGGGACTGAGA
CACGGCCCAGACTCCTACGGGAGGCAGCAGTAGGGAATCTTCGGCAATGGGGGC
AACCCTGACCGAGCAACGCCGCGTGAGTGAAGAAGGTTTTCGGATCGTAAAGCT

*Figure 11 ctd*

CTGTTGTAAGTCAAGAACGGGTGTGAGAGTGGAAAGTTCACACTGTGACGGTAG
CTTACCAGAAAGGGACGGCTAACTACGTGCCAGCAGCCGCGGTAATACGTAGGT
CCCGAGCGTTGTCCGGATTTATTGGGCGTAAAGCGAGCGCAGGCGGTTTGATAA
GTCTGAAGTTAAAGGCTGTGGCTCAACCATAGTTCGCTTTGGAAACTGTCAAACT
TGAGTGCAGAAGGGGAGAGTGGAATTCCATGTGTAGCGGTGAAATGCGTAGATA
TATGGAGGAACACCGGTGGCGAAAGCGGCTCTCTGGTCTGTAACTGACGCTGAG
GCTCGAAAGCGTGGGGAGCGAACAGGATTAGATACCCTGGTAGTCCACGCCGTA
AACGATGAGTGCTAGGTGTTGGATCCTTTCCGGGATTCAGTGCCGCAGCTAACGC
ATTAAGCACTCCGCCTGGGGAGTACGACCGCAAGGTTGAAACTCAAAGGAATTG
ACGGGGGCCCGCACAAGCGGTGGAGCATGTGGTTTAATTCGAAGCAACGCGAAG
AACCTTACCAGGTCTTGACATCCCGATGCTATTTCTAGAGATAGAAAGTTACTTC
GGTACATCGGTGACAGGTGGTGCATGGTTGTCGTCAGCTCGTGTCGTGAGATGTT
GGGTTAAGTCCCGCAACGAGCGCAACCCCTATTGTTAGTTGCCATCATTCAGTTG
GGCACTCTAGCGAGACTGCCGGTAATAAACCGGAGGAAGGTGGGGATGACGTCA
AATCATCATGCCCCTTATGACCTGGGCTACACACGTGCTACAATGGTTGGTACAA
CGAGTTGCGAGTCGGTGACGGCGAGCTAATCTCTTAAAGCCAATCTCAGTTCGGA
TTGTAGGCTGCAACTCGCCTACATGAAGTCGGAATCGCTAGTAATCGCGGATCAG
CACGCCGCGGTGAATACGTTCCCGGGCCTTGTACACACCGCCCGTCACACCACGA
GAGTTTGTAACACCCGAAGTCGGTGAGGTAACCTTTTGGAGCCAGCCGCCTAAG
GTGGGACAGATGATTGGGGTGAAGTCGTAACAAGGTAGCCGTATCGGAAGGTGC
GGCTGGATCACCT

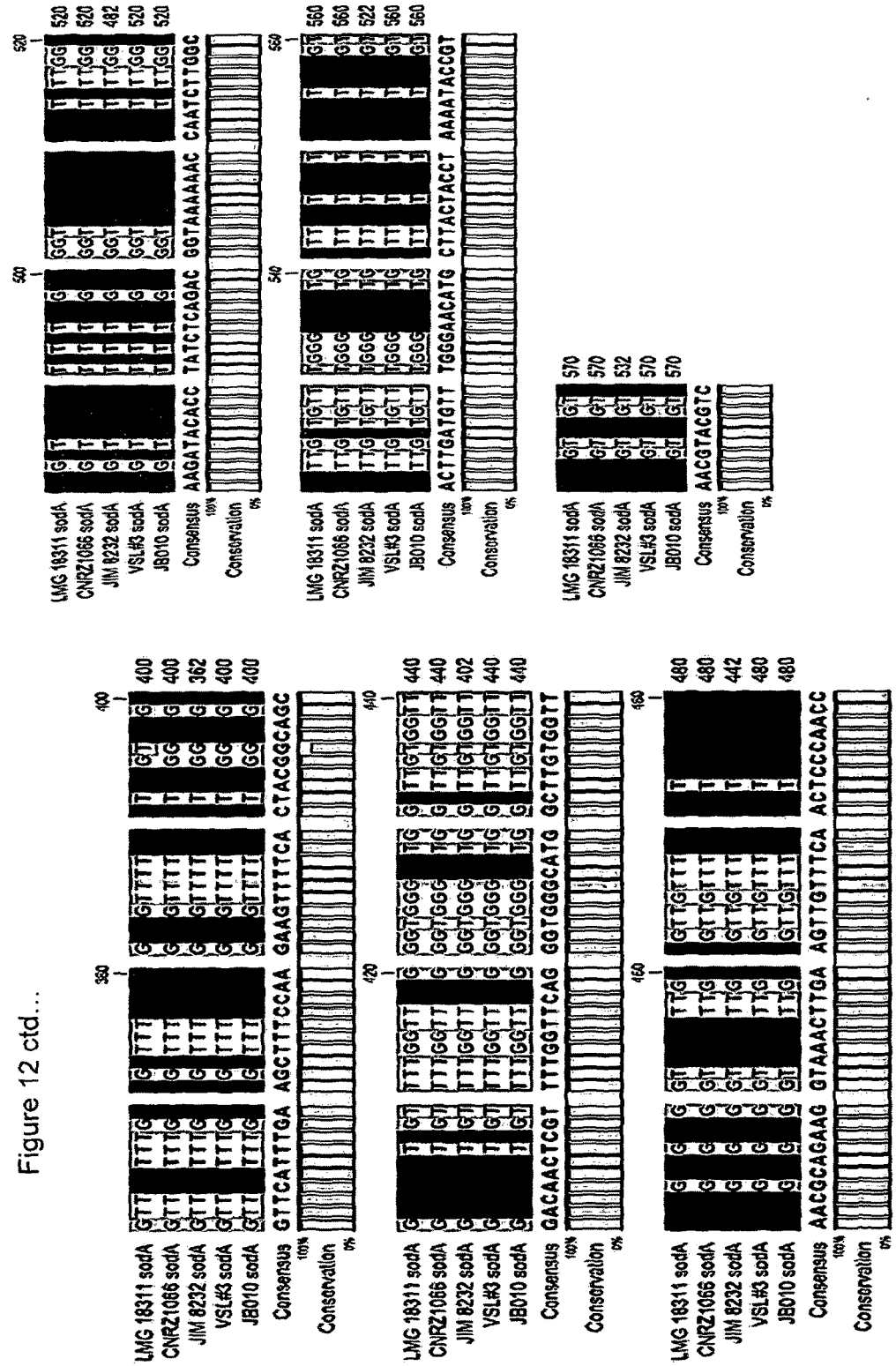
Figure 12 ctd...

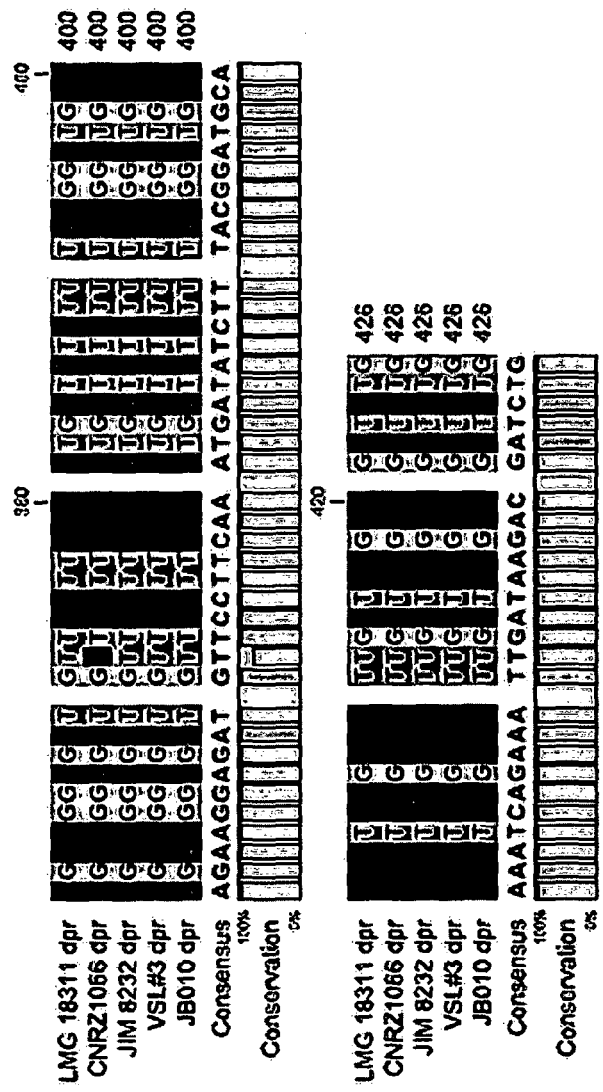
Figure 13 ctd...

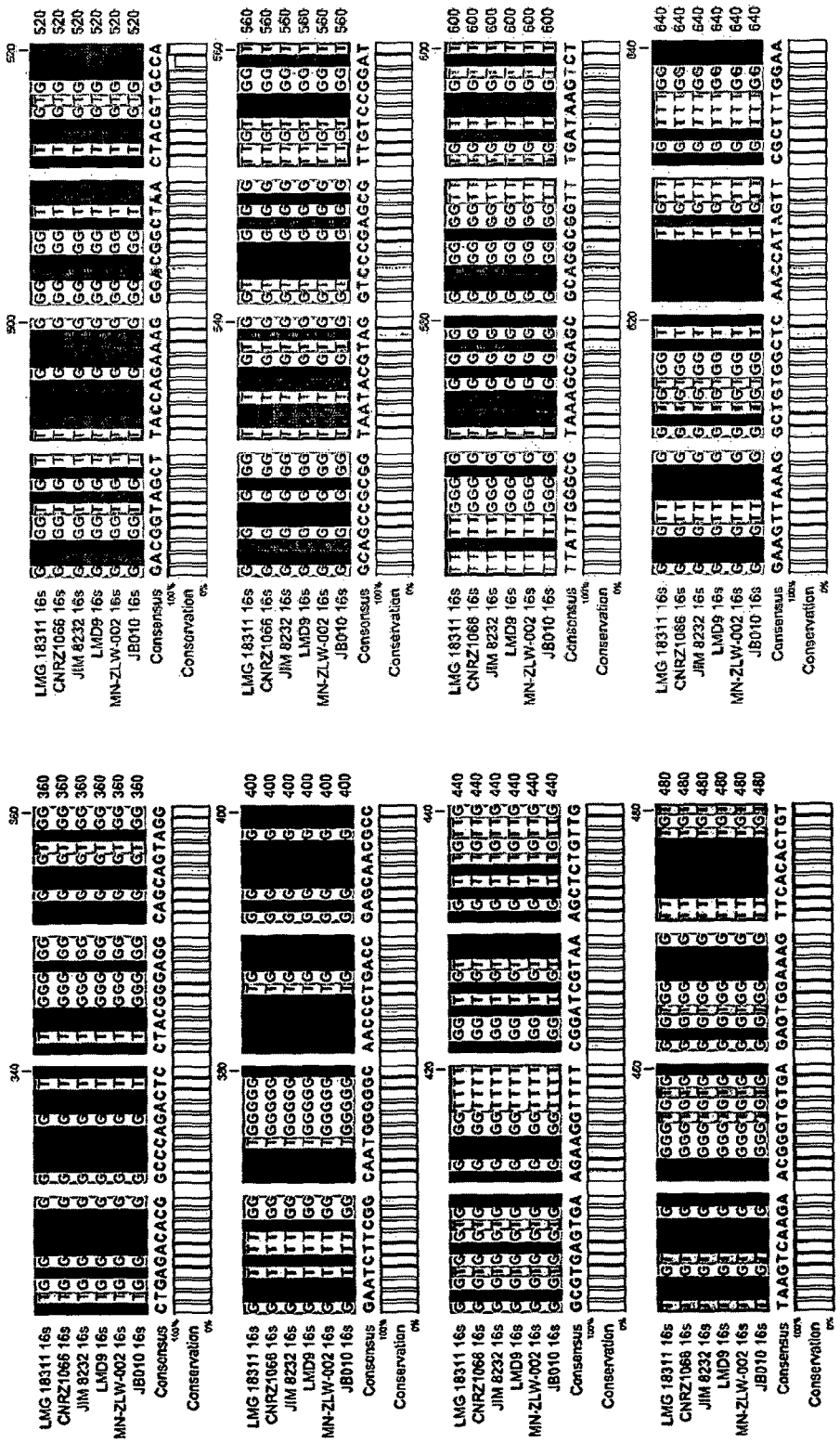
Figure 14 ctd...

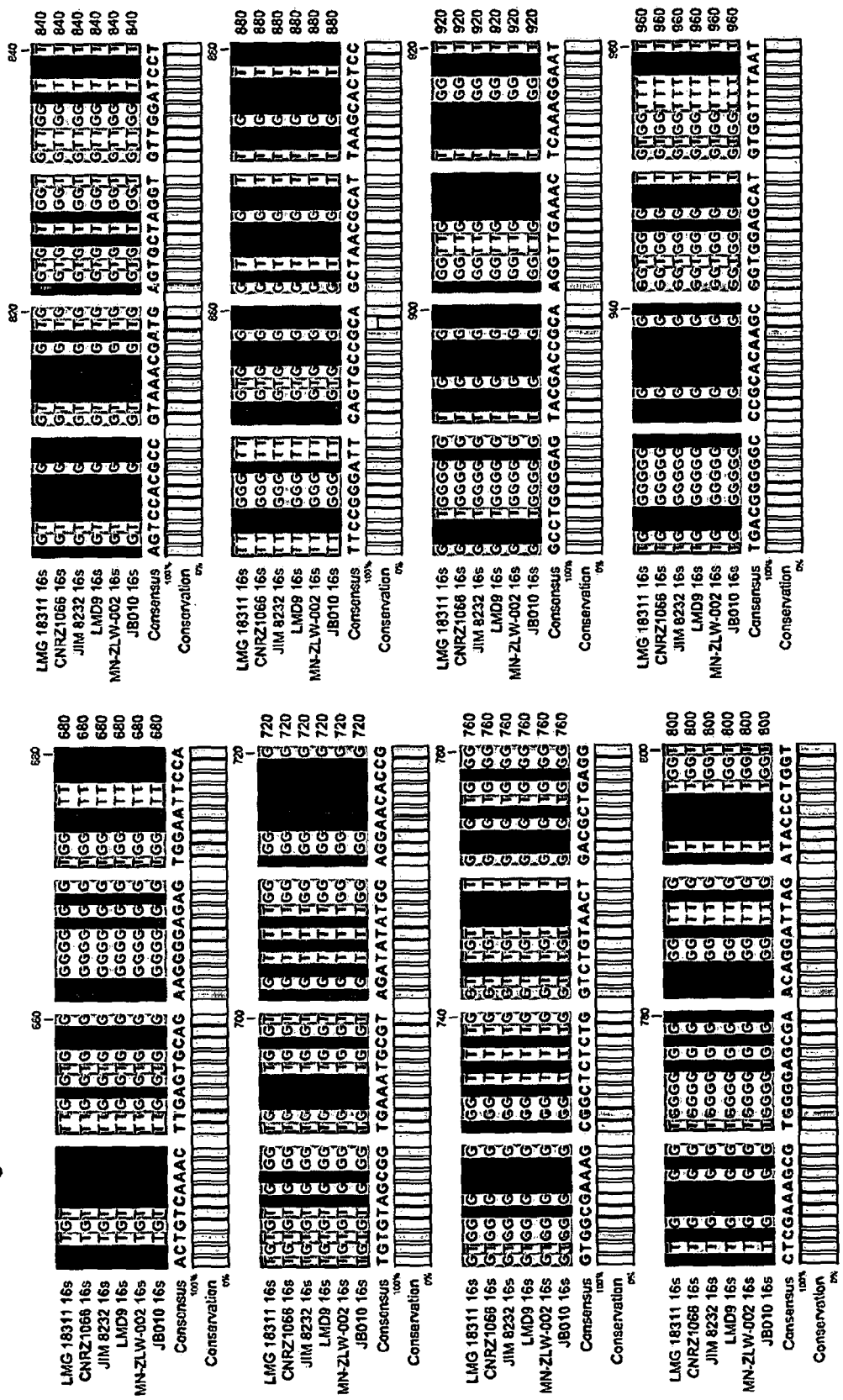
Figure 14 ctd...

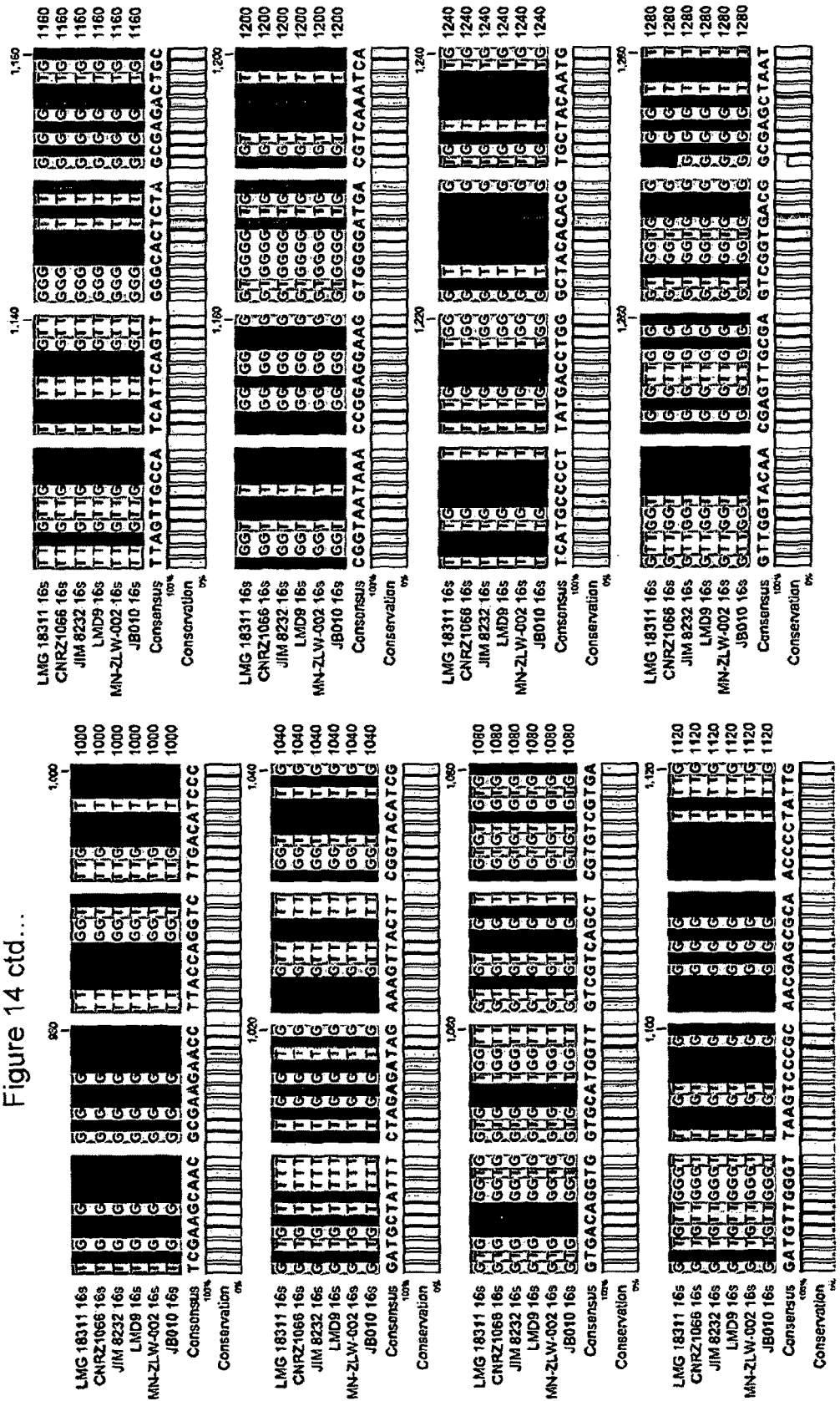
Figure 14 ctd...

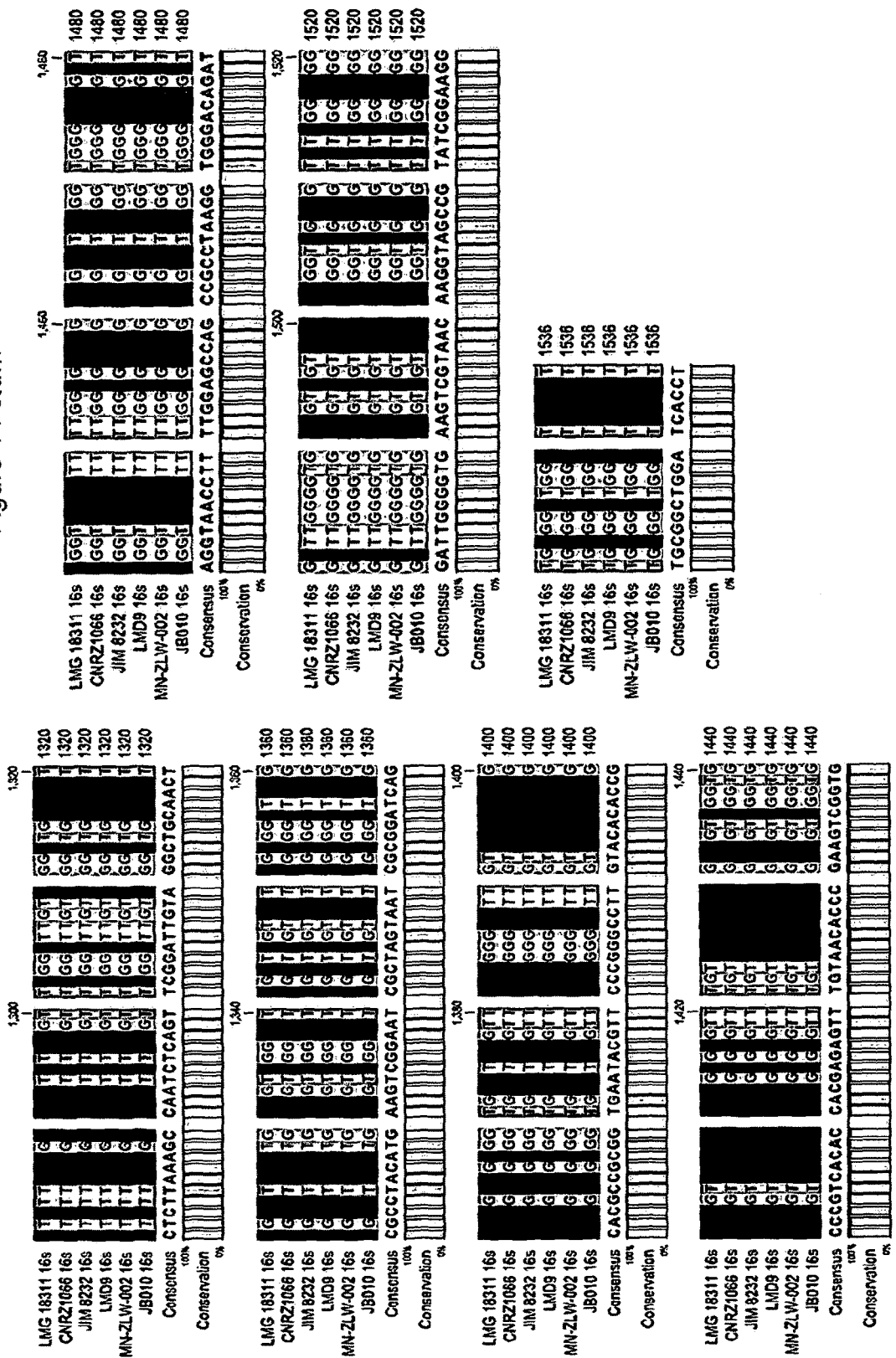

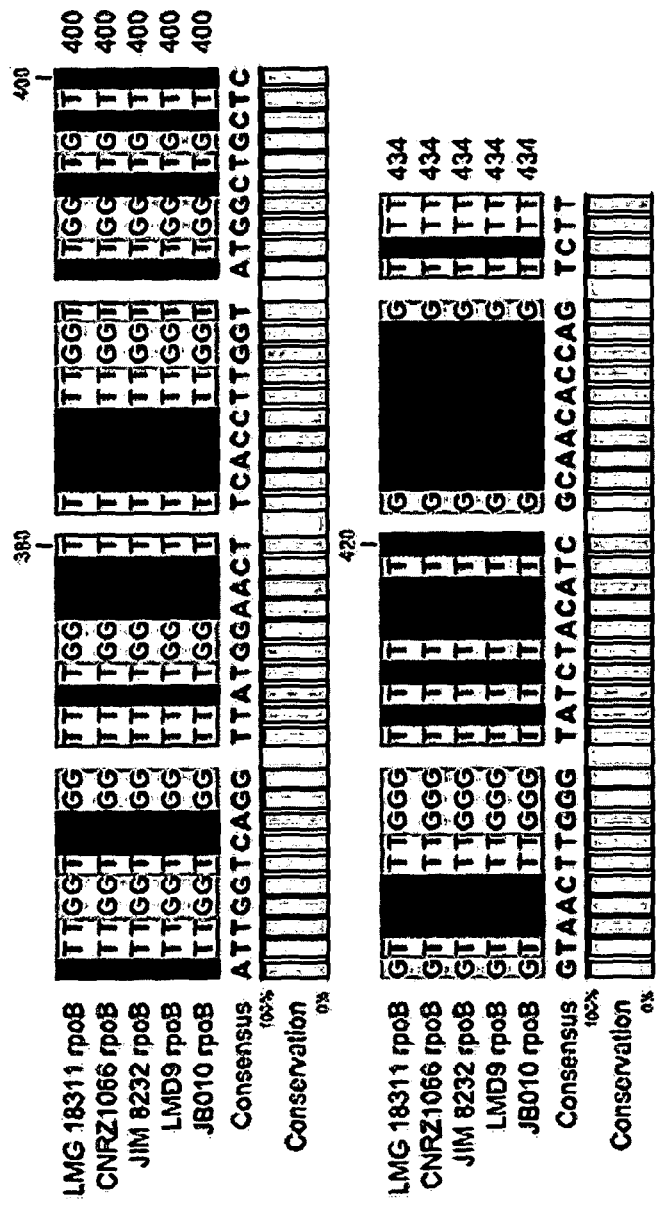
Figure 15 ctd...

Figure 16

Base changes – positions are relevant to the clipped sequence.

sodA

239: JB010 T→C
341: JB010 C→T
396: LMG 18311 G→T dpr

161: JIM 8232 & VSL#3 T→C
208: JIM 8232 & VSL#3 C→A
222: JIM8232 T→A
352: JB010 C→T
372: CNRZ1066 T→C rpoB

75: JIM 8232 A→G
345: LMD9 G→A
360: JIM 8232 & JB010 T→C

16s

182: CNRZ1066 T→C
519: LMD9 C→A
859: JIM 8232 & MN-ZLW-002 C→A
1271: LMG 18311 & CNRZ1066 G→A

SEQUENCE LISTING

```
<160> NUMBER OF SEQ ID NOS: 4

<210> SEQ ID NO 1
<211> LENGTH: 570
<212> TYPE: DNA
<213> ORGANISM: Streptococcus thermophilus NCIMB 41856
<220> FEATURE:
<221> NAME/KEY: sodA
<222> LOCATION: (1)..(570)
<223> OTHER INFORMATION: sodA gene of S. thermophilus NCIMB 41856

<400> SEQUENCE: 1
atggtaagat ggaaaaaaat gaaagagga cctttactat ggctattatt cttccagatc      60
ttccttacgc ttacgatgct ttggaaccat acattgatgc tgaaacaatg actcttcatc     120
atgacaaaca ccatgcaact tacgtggcga atgctaatgc tgcgcttgaa aaacaccctg     180
aaattggtga ggaccttgaa gcgcttttgg ctgatgtaga aaaaattcca gcagacatcc     240
gtcaagcact tattaacaat ggtggtggac atcttaacca cgcacttttc tgggaacttt     300
tgtcaccaga aaaacaagaa ccaactgcag aagtagcagc tgctattaac gaagcattcg     360
gttcatttga agctttccaa gaagttttca ctacggcagc gacaactcgt tttggttcag     420
ggtgggcatg gcttgtggtt aacgcagaag gtaaacttga agttgtttca actcccaacc     480
aagatacacc tatctcagac ggtaaaaaac caatcttggc acttgatgtt tgggaacatg     540
cttactacct aaaataccgt aacgtacgtc                                       570

<210> SEQ ID NO 2
<211> LENGTH: 426
<212> TYPE: DNA
<213> ORGANISM: Streptococcus thermophilus NCIMB 41856
<220> FEATURE:
```

```
<221> NAME/KEY: dpr
<222> LOCATION: (1)..(426)
<223> OTHER INFORMATION: dpr gene of S. thermophilus NCIMB 41856

<400> SEQUENCE: 2
gacaccaaca aacacaaaaa ccaaagcagt attaaatcaa gcggttgccg atttgtctgt      60
agcagcttct attgtgcatc aagttcattg gtatatgcgt ggtcctggtt tcctttatct     120
tcacccaaaa atggatgaat taatggatag tttgaattcc tatcttgata agattagtga     180
gcgtttgatt accattggtg gtgaacccta ctcaactttg gtagagtttt catctaattc     240
aggtttgact gaaactactg gtacatttga tcaaccaatg tctgatcgaa ttcagctatt     300
ggttgatata tacaaatact tgtctgtctt gttccaagtt ggcttggata ttacagatga     360
agaaggagat gttccttcaa atgatatctt tacggatgca aaatcagaaa ttgataagac     420
gatctg                                                               426

<210> SEQ ID NO 3
<211> LENGTH: 1536
<212> TYPE: DNA
<213> ORGANISM: Streptococcus thermophilus NCIMB 41856
<220> FEATURE:
<221> NAME/KEY: 16S
<222> LOCATION: (1)..(1536)
<223> OTHER INFORMATION: 16S gene of S. thermophilus NCIMB 41856

<400> SEQUENCE: 3
agagtttgat cctggctcag gacgaacgct ggcggcgtgc ctaatacatg caagtagaac      60
gctgaagaga ggagcttgct cttcttggat gagttgcgaa cgggtgagta acgcgtaggt     120
aacctgcctt gtagcggggg ataactattg gaaacgatag ctaataccgc ataacaatgg     180
atgacacatg tcatttattt gaaagggca attgctccac tacaagatgg acctgcgttg     240
tattagctag taggtgaggt aatggctcac ctaggcgacg atacatagcc gacctgagag     300
ggtgatcggc cacactggga ctgagacacg gcccagactc ctacgggagg cagcagtagg     360
gaatcttcgg caatggggc aaccctgacc gagcaacgcc gcgtgagtga agaaggtttt     420
cggatcgtaa agctctgttg taagtcaaga acgggtgtga gagtggaaag ttcacactgt     480
gacggtagct taccagaaag ggacggctaa ctacgtgcca gcagccgcgg taatacgtag     540
gtcccgagcg ttgtccggat ttattgggcg taaagcgagc gcaggcggtt tgataagtct     600
gaagttaaag gctgtggctc aaccatagtt cgctttggaa actgtcaaac ttgagtgcag     660
aaggggagag tggaattcca tgtgtagcgg tgaaatgcgt agatatatgg aggaacaccg     720
gtggcgaaag cggctctctg gtctgtaact gacgctgagg ctcgaaagcg tggggagcga     780
acaggattag ataccctggt agtccacgcc gtaaacgatg agtgctaggt gttggatcct     840
ttccgggatt cagtgccgca gctaacgcat taagcactcc gcctggggag tacgaccgca     900
aggttgaaac tcaaaggaat tgacgggggc ccgcacaagc ggtggagcat gtggtttaat     960
tcgaagcaac gcgaagaacc ttaccaggtc ttgacatccc gatgctattt ctagagatag    1020
aaagttactt cggtacatcg gtgacaggtg gtgcatggtt gtcgtcagct cgtgtcgtga    1080
gatgttgggt taagtcccgc aacgagcgca accctattg ttagttgcca tcattcagtt    1140
gggcactcta gcgagactgc cggtaataaa ccggaggaag gtggggatga cgtcaaatca    1200
tcatgcccct tatgacctgg gctacacacg tgctacaatg gttggtacaa cgagttgcga    1260
gtcggtgacg gcgagctaat ctcttaaagc caatctcagt tcggattgta ggctgcaact    1320
cgcctacatg aagtcggaat cgctagtaat cgcggatcag cacgccgcgg tgaatacgtt    1380
```

```
cccgggcctt gtacacaccg cccgtcacac cacgagagtt tgtaacaccc gaagtcggtg    1440
aggtaacctt ttggagccag ccgcctaagg tgggacagat gattggggtg aagtcgtaac    1500
aaggtagccg tatcggaagg tgcggctgga tcacct                              1536

<210> SEQ ID NO 4
<211> LENGTH: 868
<212> TYPE: DNA
<213> ORGANISM: Streptococcus thermophilus NCIMB 41856
<220> FEATURE:
<221> NAME/KEY: rpo
<222> LOCATION: (1)..(868)
<223> OTHER INFORMATION: rpo gene of S. thermophilus NCIMB 41856

<400> SEQUENCE: 4
cctaagggtg aaaaagacct ttctgctgaa gaacgtcttc tccatgctat ctttggtgat      60
aaatctcgtg aagtacgtga tacatcactc cgtgtacctc atggtggtga tggtgtcgtt     120
cgtgatgtta aaatctttac acgtgcaaac ggtgatgaat tgcaatcagg tgttaacatg     180
cttgttcgtg tttacatcgc tcaaaaacgt aaaatcaagg tcggagataa gatggctggt     240
cgtcacggta acaaaggggt tgtttctcgt attgttcctg ttgaagacat gccttacctt     300
ccagacggta caccagttga catcatgttg aaccctcttg gggtgccatc acgtatgaac     360
attggtcagg ttatggaact tcaccttggt atggctgctc gtaacttggg tatctacatc     420
gcaacaccag tcttcctaag ggtgaaaaag acctttctgc tgaagaacgt cttctccatg     480
ctatctttgg tgataaatct cgtgaagtac gtgatacatc actccgtgta cctcatggtg     540
gtgatggtgt cgttcgtgat gttaaaatct ttacacgtgc aaacggtgat gaattgcaat     600
caggtgttaa catgcttgtt cgtgtttaca tcgctcaaaa acgtaaaatc aaggtcggag     660
ataagatggc tggtcgtcac ggtaacaaag gggttgtttc tcgtattgtt cctgttgaag     720
acatgcctta ccttccagac ggtacaccag ttgacatcat gttgaaccct cttggggtgc     780
catcacgtat gaacattggt caggttatgg aacttcacct tggtatggct gctcgtaact     840
tgggtatcta catcgcaaca ccagtctt                                        868
```

PROBIOTIC FORMULATION

This invention relates to a probiotic formulation. More particularly, the present invention describes a probiotic organism which is capable of proliferation in an environment which is generally unfavourable to probiotic organisms.

Probiotics are organisms, generally bacteria, which are considered to be beneficial rather than detrimental to their animal host. In terms of digestive health the concept of consuming beneficial bacteria has been popular in recent years, even though the benefit of consuming specific strains of bacteria was first proposed by Elie Metchnikoff in 1907. He suggested that since lactic acid bacteria can prevent putrefaction of stored food, they may also benefit the gastrointestinal tract; *Bulgarian bacillus* (later identified as *Lactobacillus delbruickii* subspecies *bulgaricus*) isolated from a fermented milk product was of particular interest. Metchnikoff proposed it was the optimal strain to consume because of its ability to produce large amounts of lactic acid with little succinic or acetic acid; its ability to coagulate milk rapidly; and the lack of alcohol and acetone produced (1). Interest in probiotics waned with the advent of antibiotics. However, with the emergence of antibiotic-resistant bacteria, there is renewed interest in probiotic bacteria, which are now defined as "live microorganisms which when administered in adequate amounts confer a health benefit on the host" (2). It is now a popular concept that the accumulation of probiotic organisms in the gut is beneficial to the general health of the host organism and there are reports which indicate that the administration of probiotics is useful in the treatment of intestinal disease.

For example, following on from Metchnikoff's work, probiotics, particularly *Lactobacillus* spp., have been trialled in the treatment of a number of diseases. *Lactobacillus* spp. probiotics have also been successful in the treatment of acute infectious diarrhoea in children (3) and prevention of traveller's diarrhoea (4) and antibiotic-associated diarrhoea (AAD) (5), but not Crohn's disease (6). In contrast, two probiotic preparations which are not based upon *Lactobacillus* spp., VSL#3 and *Escherichia coli* Nissle 1917, have been reported as showing promise in the treatment of inflammatory bowel disease (IBD) (7-10). Crohn's disease is considered to be a response to an environmental trigger in a genetically susceptible host. The environmental trigger is thought to be bacteria and current research is now focused on adherent-invasive *E. coli* (AIEC) (11). The present inventors considered that if Crohn's disease is indeed triggered by bacteria then it is an attractive candidate for treatment with a probiotic which could either outcompete the triggering bacteria or could divert the immune response in order to prevent the uncontrolled inflammation which is a characteristic feature of Crohn's disease and other inflammatory bowel conditions. However, in order for any probiotic to carry out either of these functions it must be able to survive and compete within this challenging environment.

Other bacteria, have been described as having iron-tolerance such as the *S. thermophilus* described by Sieuwerts et al (38) by Herve-Jimenez et al (39) and by Simova et al (37). However, when discussing the noted differential expression of iron transport protein genes Sieuwerts (38) describes that this is a hydrogen peroxide response and the use of that *S. thermophilus* in co-culture showed no iron-responsive effect. Simova (37) describes that the presence of iron fortification or the concentration of ferrous lactate had no significant effect on the time taken to reach pH 4.5 and hence on growth rates. The present inventors tested the strain described by Herve-Jimenez et al (39) and found that this strain was not iron-responsive (strain BAA250 in FIG. 17).

In this respect the present inventors noted that the *Lactobacillus* spp. probiotics in general use were not generally capable of surviving and competing in the hostile environment of the inflamed intestine associated with such diseases, and especially in the presence of iron from blood in the inflamed intestine. The present inventors set out to further investigate this observation.

The lactic acid bacteria (LAB) are unusual organisms in that they do not appear to have a requirement for iron (12-14) whilst maintaining a high demand for manganese (15). In the human body, iron is sequestered by the transferrins and lactoferrin (16). Iron sequestration is considered the primary factor limiting bacterial growth rate in the body. An increase in the availability of iron in the intestine by dietary supplementation, intestinal bleeding, surgery, trauma or when under stress, will lead to an increase in the abundance of many bacterial species. This is mediated by a greater availability of free iron, or by the presence of noradrenaline, which unloads iron from chelators and can supply it to some species of bacteria (17-18). Under these high-iron conditions, LAB are rapidly outcompeted as other species increase their growth rate in response to iron availability and predominate. Thus, the present inventors determined that for adequate or therapeutic levels of probiotic bacteria to be maintained under high iron conditions they must be able to respond to this element by increasing growth rate in order to compete with the normal flora. They then postulated that an inability to compete with potential pathogens under conditions of stress and trauma, and especially under those conditions which result in increased iron levels, may contribute to the lack of efficacy shown by many LAB-based probiotics in treating disease.

As will be described below, the present inventors have shown that the majority of LAB do not respond to noradrenaline-mediated iron availability by increasing growth rate. Many intestinal diseases, both chronic and acute, are associated with intestinal bleeding which will lead to higher levels of iron being present in the intestine. Therefore, this will not present a suitable environment for colonisation by conventional LAB-based probiotics, further contributing to the lack of efficacy seen with many conventional LAB-based probiotics in treating such diseases.

Having identified this previously unseen problem, the present inventors then investigated the possibility of identifying a probiotic which was in fact able to increase growth rate in response to iron availability. The present inventors thus identified and selected species of bacteria that can increase growth rate under these conditions.

Accordingly, the present invention provides a *Streptococcus thermophilus* spp. which is able to increase growth rate in response to increased iron availability especially in a competitive in vivo environment where there is competition for food and other requirements for growth and reproduction.

Advantageously, the *Streptococcus thermophilus* spp. of this invention present an alternative to the traditional LAB spp. probiotics, because they are, in fact, active and functional in the mixed culture population encountered in the true gut environment even during periods of increased iron concentration from intestinal bleeding, trauma, stress or other factors. Hence, the *Streptococcus thermophilus* spp. of the present invention are suitable for use in the treatment of intestinal diseases in general and especially for use in those diseases associated with or complicated by elevated iron levels resulting from, for example, the presence of blood due to intestinal bleeding or leaking epithelia or from the presence of supplemented iron from a nutritional supplement or fortified food.

The *Streptococcus thermophilus* spp. of the present invention is preferably able to sustain its increase in growth rate in a mixed population environment in the presence of iron for more than one day and more preferably for several days. It is preferred that the *Streptococcus thermophilus* spp. of the present invention is able to grow and compete with other gut bacteria, such as commensal organisms but especially in the presence of pathogenic bacteria, at the concentrations of iron which may be encountered during periods of intestinal bleeding.

In a most preferred embodiment the *Streptococcus thermophilus* spp. is able to survive, reproduce and grow in an iron-rich growth medium in the presence of other organisms for a time equivalent to that of normal digestive transit, such as at least one and up to three days. More preferably, the *Streptococcus thermophilus* spp of the present invention is able to grow in the presence of endogenous and pathogenic bacteria in a hostile or diseased gut environment as well as in a healthy gut environment. A "hostile" gut environment is intended to describe a gut environment in which probiotic organisms generally struggle to compete with other organisms and hence either have a lower growth rate or are unable to survive. Examples, not intended to be limiting, of a hostile gut environment, include the presence of blood, the presence of artificially induced levels of minerals, especially iron, and vitamins, for example from a supplement, the presence of chelating agents, the presence of drugs or other medications which impact on the gut environment, changes caused by chronic gastro-intestinal disease, and changes induced hormonally, such as stress.

It is preferred that the *Streptococcus thermophilus* spp. of the present invention is tolerant of low pH to enable passage through the stomach during digestion and accordingly it is preferred that the *Streptococcus thermophilus* spp. is able to survive at a pH of 2. More preferably, the *Streptococcus thermophilus* spp. is able to survive at a pH below 2 such as 1.5 or even lower. Even more preferably, this is achieved in a mixed population environment such as that encountered in vivo. Alternatively, to overcome problems associated with low gastric pH the *Streptococcus thermophilus* spp. may be provided in a formulation which is in itself resistant to low gastric pH, such as being provided with a digestion-resistant or enteric coating especially when in tablet or capsule form. Such a coating may be of conventional type for a capsule, tablet or the like for oral delivery.

In a most preferred embodiment the *Streptococcus thermophilus* spp. is able to survive, reproduce and grow in a low pH growth medium equivalent to typical gastric pH for at least the time typical of gastric transit which is about two hours. Even more preferably, this is achieved in a mixed population environment such as that encountered in vivo.

The *Streptococcus thermophilus* spp. of the present invention is known by the internal designation of *Streptococcus thermophilus* JB010. *Streptococcus thermophilus* JB010, the preferred *Streptococcus thermophilus* spp., of the invention may be identified by whole or partial DNA sequencing, such as randomly amplified polymorphic DNA (RAPD) analysis where the primers M13 and MSP were used to randomly amplify DNA fragments from *S. thermophilus* strains. The unique banding pattern generated by *S. thermophilus* JB010 demonstrates genetic differences between this strain and all other strains examined. This shows that the *Streptococcus thermophilus* spp. of the present invention is different to the commercially available strain VSL#3. The details of this RAPD analysis will be set out in more detail in the Examples which follow.

The *Streptococcus thermophilus* spp. of the present invention has been deposited with NCIMB Ltd. (Ferguson Building Craibstone Estate, Bucksburn, Aberdeen, AB21 9YA UK, an International Depositary Authority registered under the Budapest Treaty) on Jul. 6, 2011, under the accession number NCIMB 41856.

Hence, the present invention also provides the *Streptococcus thermophilus* NCIMB 41856.

The *Streptococcus thermophilus* spp. of the present invention may be provided in a composition suitable for use as a food, a food supplement, a nutraceutical or as a therapeutic. Such a composition may be based on a milk product, as is conventional for probiotics. The milk product is preferably a fermented milk product such as yoghurt. The composition may contain the *Streptococcus thermophilus* spp. as the sole probiotic ingredient, as the major probiotic or may contain a mixture of probiotics. Non-dairy formulations, formulations based on milk-alternatives such as soya milk and yoghurts, fruit-based formulations and the like are also contemplated as food supplements. Especially where the composition is a food supplement, the composition may comprise other ingredients such as flavourings or other conventional food ingredients to improve the taste, palatability, texture or other organoleptic properties of the composition.

Alternatively, the *Streptococcus thermophilus* spp. of the present invention may be provided in the form of a powder, capsule, tablet or the like, and hence the conventional ingredients for that delivery system will be present, for example, gelatin, cellulose, starches, excipients, binders, flavours, anti-caking agents, preservatives and other pharmaceutically acceptable delivery vehicles and ingredients.

Accordingly, the present invention provides a food, a food supplement, nutraceutical or a therapeutic comprising a *Streptococcus thermophilus* spp. which is able to increase growth rate in response to iron availability.

More specifically, the present invention provides a food, a food supplement, nutraceutical or a therapeutic comprising *Streptococcus thermophilus* NCIMB 41856.

It is envisaged that the present invention will be usable in the treatment of intestinal diseases, especially those associated with an increase in the availability of iron in the intestine due to intestinal bleeding, surgery, trauma or under stress. Such diseases may be chronic, for example, inflammatory bowel diseases, such as Crohn's disease or ulcerative colitis, irritable bowel syndrome, coeliac disease, gastroenteritis or pancreatitis, or they may be acute such as injury, surgery, infection (for example *C. difficile* infection) or infestation by protozoa or worms.

The food, food supplement, nutraceutical or a therapeutic may be provided in a formulation suitable for use in humans or in animals.

In a most preferred embodiment the *Streptococcus thermophilus* spp. of the present invention is also able to act locally to reduce the level of chronic inflammation in the gut. This is preferred since it allows the adaptive immune system to clear any infection in a controlled manner and promotes regulation and resolution of gut inflammation.

The mechanisms through which probiotics have been hypothesised to act are numerous and include an influence on intestinal transit time, competition with pathogens and immune modulation. It is not clear what effect on the immune system is most desirable. A pro-inflammatory response may be required in order to more effectively clear infection (19-20), however prolonged NF-κB activation, and subsequent production of IL-8, RANTES and CXCL10, has been implicated in animal models of IBD (21). In contrast, probiotic strains of bacteria have been shown to act specifically on components of the adaptive immune response in order to reduce inflammation and promote regulation. *Faecalibacterium prausnitzii* is a probiotic strain capable of reducing the expression of the pro-inflammatory cytokines IL-12 and IFNγ by PBMCs (22.). Upregulation of regulatory IELs in a mouse model of colitis was induced by two mixtures of probiotics: *L. acidophilus* and *B. longum*; *L. plantarum*, *S. thermophilus* and *B. animalis* subsp. *lactis* (23). Furthermore, a combination of *L. acidophilus*, *L. casei*, *L. reuteri*, *B. bifidum* and *S. thermophilus* downregulated Th1, Th2 and Th17 cytokine responses, induced generation of CD4$^+$ Foxp3$^+$ Tregs and promoted regulatory dendritic cells expressing high levels of the regulatory cytokines IL-10 and TGFβ(24).

As set out above, LAB have uniquely very low requirements for iron (12-14). The increased bioavailability of iron during intestinal bleeding can increase the growth rate and virulence of many gastrointestinal pathogens (25); under these conditions, LAB can be outcompeted. The results obtained by the present inventors indicate that most LAB cannot respond to increased iron bioavailability (see Table 1 below), with the exception of *Lactobacillus acidophilus* ASF360 and the *Strep. thermophilus* of the present invention, *Streptococcus thermophilus* NCIMB 41856. It is thought that one of the principal mechanisms for the action of probiotics is competitive exclusion of pathogens. The results of the present inventors support their theory that LAB-based probiotics are inefficient during active inflammatory disease because of their inability to compete with pathogens in the presence of iron, due to bleeding or supplementation.

For a probiotic to be effective in treating IBD, the present inventors consider that it must be able to effectively compete with pathogens under the conditions encountered in the non-healthy intestine. It should also be able to control immune responses to pathogens and restore normality. These are the primary properties that were investigated in this work. Using a rational selection process the present inventors determined that the iron-responsive strain of *S. thermophilus* NCIMB 41856 shows probiotic potential. This *S. thermophilus* NCIMB 41856 performed at least as well, and in many cases, better than, the more widely researched strains of *L. acidophilus* and *E. coli* Nissle 1917. *E. coli* is known to be able to respond to iron (25), and the present inventors have shown that *S. thermophilus* JB010 (NCIMB 41856) can also respond to iron (Table 1). However, whereas the present inventors have now found that *S. thermophilus* JB010 (NCIMB 41856) promoted an anti-inflammatory response, they found that, consistent with the findings of other groups (26), *E. coli* Nissle 1917 provoked a pro-inflammatory response from gut and gut-derived cells and cell lines. The present inventors' have hypothesised that activation of epithelial cells, as demonstrated here by the ability of *E. coli* Nissle 1917 to induce an NF-κB and IL-8 response, leads to an increase in innate immune defenses, thereby improving barrier function (27). However, concerns have been raised about the safety of *E. coli* Nissle 1917 as a probiotic, particularly in immunocompromised patients (28).

The results presented here show that the present inventors' strain of *S. thermophilus*, (NCIMB 41856, also designated JB010), is a promising probiotic in the in vitro experiments. *S. thermophilus* has largely been overlooked as a probiotic strain of bacteria in favour of *Lactobacillus* or *Bifidobacterium* spp and little work has been done to determine the mode of action of this probiotic. Despite this, *S. thermophilus* spp. is a constituent of the VSL#3 probiotic preparation, which is one of the few probiotic therapies to have a significant effect on the treatment of IBD (10). The advertising literature for VSL#3 suggests that it is the combination or blend of the eight strains of bacteria which make up VSL#3 together with the increase in the numbers of bacteria present in a single dose of the product which provide this beneficial effect by providing the "optimal intestinal flora". Additionally, the present inventors have shown that the *S. thermophilus* present in VSL#3 is not iron responsive in the same manner as the *S. thermophilus* NCIMB 41856 of the present invention.

The present inventors have also shown by RAPD DNA analysis, as described below, that their strain of *S. thermophilus* (*Streptococcus thermophilus* NCIMB 41856) is not the same as that present in VSL#3 (See FIG. 10 which shows the difference in the DNA analysis between the two).

The present inventors have also determined the partial gene sequences of the sodA, dpr, 16S and rpoB genes of *Streptococcus thermophilus* NCIMB 41856 and have determined, by alignment, that they differ from the same sequences in the lactic acid bacteria strains LMG 18311, CNRZ1066, JIM 8232, and VSL#3 (See FIGS. 11-16). The sodA and dpr genes have been associated with iron and/or manganese usage in bacteria, especially LAB, while the 16S and rpoB genes are representative of bacterial lineage.

*S. thermophilus* is also present in the majority of fermented milk products, some of which have been successfully used as therapeutic treatments (29); however the levels of this bacterial spp. present in those products are too low to have a probiotic effect (30). The present inventors have found that the beneficial effect exerted by *Streptococcus thermophilus* NCIMB 41856 is dose-dependent, with the optimum in vitro dose being 1000 times more concentrated than that found in the majority of fermented milk products previously trialled. Few studies have looked into the probiotic effect of *S. thermophilus* alone, however, it was reported that milk fermented with this strain of bacteria was equivalent to proton-pump inhibitors in reducing gastritis induced by non-steroidal anti-inflammatory drugs (31).

The present inventors believe that the predominant effect of *S. thermophilus* J8010 (NCIMB 41856) would be in reducing inflammation in the gut, firstly exerting its effects from the lumen of the gut and secondly, when intestinal barrier function is compromised, by crossing through the epithelium and interacting with the underlying cells. Here the present inventors have shown that this probiotic strain of bacteria is capable of reducing epithelial cell death as well as the NF-κB and IL-8 response to pathogen, thereby limiting the pro-inflammatory response initiated by the innate immune system. Furthermore, it acts on the adaptive immune system by modulating the T cell response, promoting regulation and reducing inflammation. The pro-inflammatory response to pathogenic *E. coli* was essentially cancelled out by the addition of *Streptococcus thermophilus* NCIMB 41856, returning levels of the varying T cell subsets to those seen under normal conditions in the present inventors' ex vivo system. This was further emphasised by the ability of *S. thermophilus* J8010 (NCIMB 41856) to reduce the transcription of mRNA encoding TNFα in response to AIEC. As previously mentioned, AIEC has been implicated in the pathogenesis of Crohn's disease, therefore the ability of *S. thermophilus* J8010 (NCIMB 41856) to reduce the production of TNFα, the principle pro-inflammatory cytokine present in this condition, is highly important.

In conclusion, *S. thermophilus* J8010 (NCIMB 41856) is an iron-responsive probiotic strain of bacteria with far-reaching applications, capable of reducing egress of pathogenic bacteria from the lumen of the gut, improving barrier function and reducing gut inflammation.

Accordingly, in a second aspect, the present invention provides a *Streptococcus thermophilus* spp. which is able to act locally to reduce the level of chronic inflammation in the gut.

Hence, the present invention provides *Streptococcus thermophilus* NCIMB 41856 for use in a medicament for the reduction of chronic inflammation in the gut.

In a preferred embodiment, the same *Streptococcus thermophilus* spp. is also able to increase growth rate in response to iron availability. Preferably, this is *Streptococcus thermophilus* NCIMB 41856

In the most preferred embodiment, the two aspects of the invention are provided by the same probiotic, *Streptococcus thermophilus* NCIMB 41856.

Embodiments of the invention will now be described with reference to and as illustrated by the accompanying drawings of which FIG. 1 is a series of graphs illustrating the effect of probiotics on proliferation and death of epithelial cells in response to pathogenic *E. coli*. a) Proliferation of T84 cells; b) proliferation of Caco-2 cells; c) death of T84 cells; d) death of Caco-2 cells. Results are shown from 3 replicate experiments and are expressed as mean±S.E.M. * $p \leq 0.05$,  $p \leq 0.01$ and * $p \leq 0.001$;

FIG. 2 is a series of graphs further detailing the results shown in FIG. 1 for Caco-2 cells illustrating the change in TEER in response to *E. coli* and the effect of probiotic on this response. * $p \leq 0.05$,  $p \leq 0.01$ and * $p \leq 0.001$;

FIG. 3 is a series of graphs further detailing the results shown in FIG. 1 for T84 cells illustrating the change in TEER in response to *E. coli* and the effect of probiotic on this response. * $p \leq 0.05$,  $p \leq 0.01$ and * $p \leq 0.001$;

FIG. 4 is a series of graphs illustrating the effect of probiotics on NF-κB (a) and IL-8 (b) response to pathogen. Results are shown from 6 replicate experiments and are expressed as mean±S.E.M. * $p \leq 0.05$,  $p \leq 0.01$ and * $p \leq 0.001$;

FIG. 5 is a series of graphs illustrating the percent change in cytokine mRNA levels induced by T cells in response to *E. coli* with and without probiotic. Results are expressed as mean±S.E.M. * $p \leq 0.05$;

FIG. 6 is a series of graphs illustrating the translocation of bacteria through a Caco-2 or T84 epithelial cell monolayer. Results are shown from 3 replicates and are expressed as means. * $p \leq 0.05$,  $p \leq 0.01$ and * $p \leq 0.001$;

FIG. 9 is a series of graphs illustrating the percent change in cytokine mRNA levels induced by T cells in response to *E. coli* with and without probiotic. Results are expressed as mean±S.E.M. * $p \leq 0.05$ and ** $p \leq 0.01$;

FIG. 10 is a photograph of a gel showing the DNA fragments produced following RAPD PCR;

FIG. 11 shows the sequence listing of the sodA, dpr, 16S and rpoB genes of *Streptococcus thermophilus* NCIMB 41856;

FIG. 16 shows the specific base changes between the lactic acid bacterial strains LMG 18311, CNRZ1066, JIM 8232, VSL#3, and JMB010 (*Streptococcus thermophilus* NCIMB 41856) in the sodA, dpr, 16S and rpoB (lineage) genes;

Figure 17:
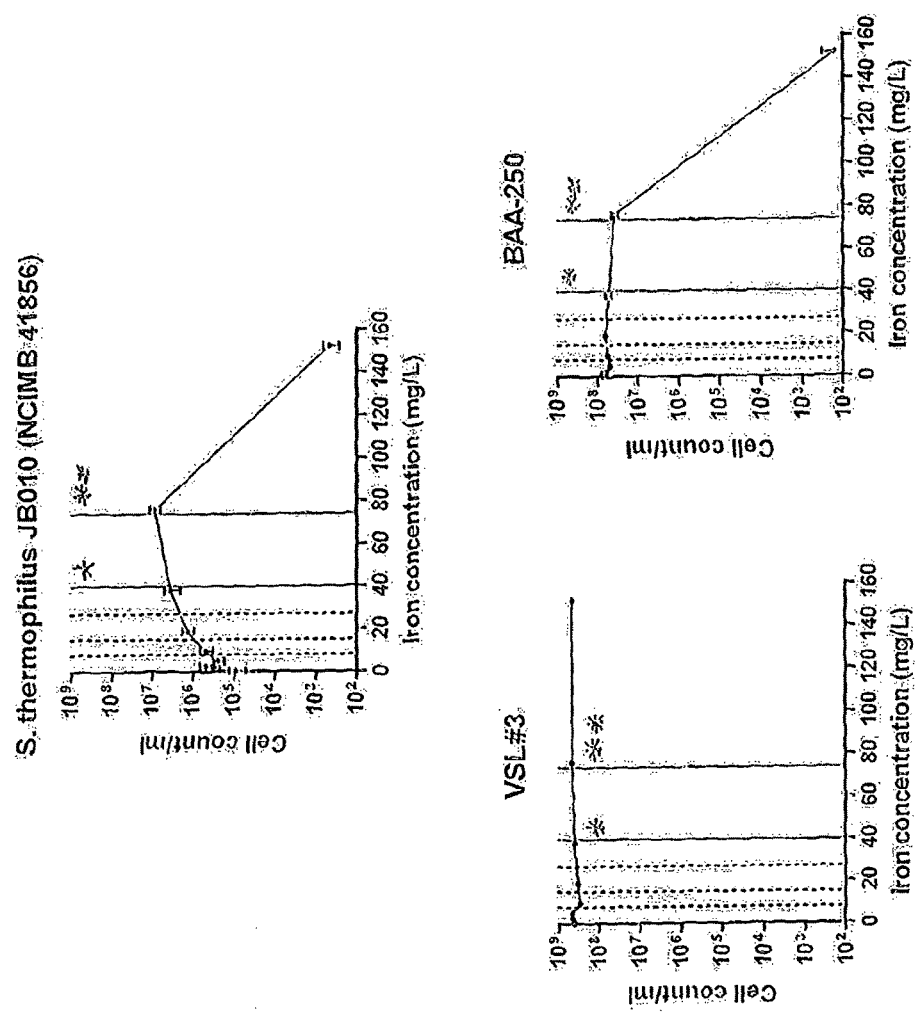
Figure 18:
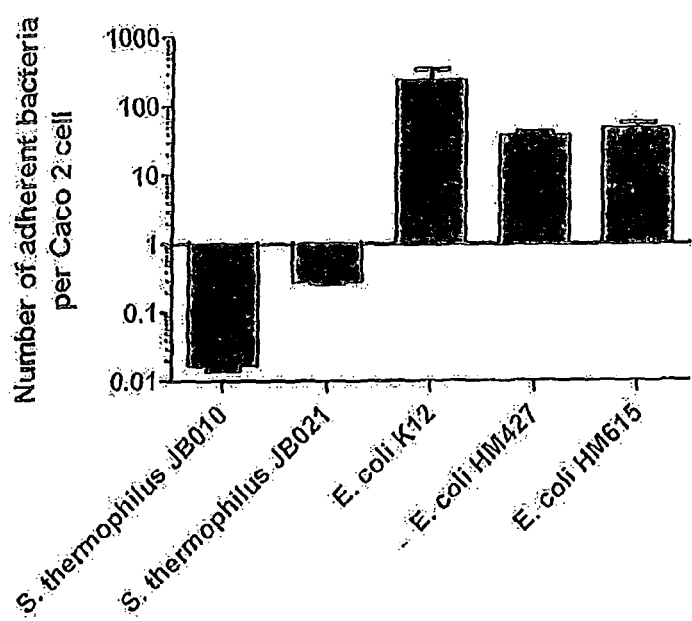

FIG. 17 is a graph showing the growth response rates of JMB010 (*Streptococcus thermophilus* NCIMB 41856) and VSL#3 and BAA-250 in the presence of iron where the blue line (*) defines the mean level of iron in faeces of people not taking iron supplements and the red line () defines the mean level of iron in the faeces of people taking iron supplements, and the dotted lines represent the level of iron used to fortify yoghurt in the description of Simova et al (37), and FIG. 18** is a graph showing the adherence of the bacterial strains *S. thermophilus* JB010 (*Streptococcus thermophilus* NCIMB 41856), *S. thermophilus* JB021, *E. coli* K12, *E. coli* HM427, and *E. coli* HM615 to Caco 2 cells.

EXAMPLES

Bacteria

Species of lactic acid bacteria that have been employed as probiotics were used. These were: *L. bulgaricus* JB005, *L. casei* JB006, *L. casei* JB008, *B. animalis* JB007, and *B. bifidum* JB009 (isolated from yoghurt by the present inventors); *L. plantarum* JB011 and *L. helveticus* JB012 (isolated by the present inventors from probiotic capsules); and the commensal isolates *L. acidophilus* ASF360 and *L. salivarius* ASF361 (components of the Schaedler flora). Two strains of *S. thermophilus* (JB004 and JB010 [*Streptococcus thermophilus* NCIMB 41856]) were isolated from yoghurt by the present inventors. Two strains of AIEC were used: HM427 and HM615 (kindly provided by Dr Barry Campbell and Prof Jon Rhodes, University of Liverpool), as was *E. coli* K12 and *E. coli* Nissle 1917 (isolated from Mutaflor (Ardeypharm GmbH, Herdecke, Germany)). All *E. coli* strains were grown in 10 ml volumes of LB broth (Oxoid, Cambridge, UK) at 37° C. overnight. *S. thermophilus* was grown in M17 broth supplemented with lactose (Oxoid) and *Lactobacillus* spp were cultured in MRS broth (Oxoid) overnight in a microaerobic atmosphere. Lactic acid bacteria were cultured in serum-SAPI medium with and without 100 µM (−) noradrenaline (Sigma, Poole, UK) in order to determine if they were capable of responding to it. O.D. measurements were taken at 24, 48 and 72 hours in order to determine bacterial growth. Differences were analysed using a repeated-measures ANOVA.

Identification of *Streptococcus thermophilus* NCIMB 41856

The *Streptococcus thermophilus* spp. NCIMB 41856 was determined to be different to the known from VSL#3 strain by using randomly amplified polymorphic DNA (RAPD) analysis where the primers M13 and MSP were used to randomly amplify DNA fragments from various *S. thermophilus* strains. The unique banding pattern generated by *S. thermophilus* NCIMB 41856 demonstrates genetic differences between this strain and all other strains examined, including VSL#3 (see FIG. 10).

RAPD

The analysis of randomly amplified polymorphic DNA (RAPD) is a technique used to determine interspecies differences in *S. thermophilus* isolates. Two sets of previously described primers, M13 (5'-gagggtggcggttct-3') and MSP (5'-gtaaaacgacggccagt-3') (36), were used collectively to produce random fragments which generate a characteristic fingerprint pattern following gel electrophoresis. DNA was extracted from *S. thermophilus* isolates by resuspending a small sweep of colonies in 500 µl nuclease-free water and heating to 100° C. for 10 minutes. PCR was performed using GoTaq Hot Start Polymerase (Promega), 0.2 µM of each primer and 5 µl DNA in a final volume of 25 µl per reaction. Magnesium chloride concentrations were adjusted to 7.2 mM in the final reaction by the addition of 50 mM $MgCl_2$. Sample incubations were performed in a DNA Engine DYAD Peltier Thermal Cycler (MJ Research) at 95° C. for 2 minutes and then 60 cycles of 94° C. for 30 seconds, 45° C. for 30 seconds and 72° C. for 80 seconds followed by a final period of 4 minutes at 72° C. PCR products were run out on a 1.5% agarose gel in order to visualise DNA fragments. The results are shown in FIG. 10 in which the control is the PCR mix water and contains a band amplified from residual *E. coli* DNA present in the PCR mix.

Proliferation and Death of Epithelial Cells

Increased turnover of epithelial cells is a common response to infection therefore we assessed the effect of pathogenic *E. coli* on the proliferation and death of epithelial cell lines and the effect of probiotic on this. All cell culture reagents were purchased from PAA Laboratories (Austria) unless otherwise specified. T84 (an intestinal cell metastasised to the lung) and Caco-2 (colonic) human adenocarcinoma cells were grown in DMEM/Ham's F-12 or DMEM respectively, supplemented with 10% FCS, 2 mM L-glutamine and 100 U/ml penicillin/streptomycin in 96-well tissue culture plates at an initial density of $2.4 \times 10^4$ cells per well. After 3 days incubation, the medium was changed for one that was antibiotic-free and cells were labelled with BrdU in order to quantify proliferation. Bacteria were added to the epithelial cell cultures at an MOI of 30 and incubated for 24 hours at 37° C. with 5% $CO_2$. After 24 hours supernatants were harvested to determine cytotoxic effects of bacteria using the Cytotox 96 non-radioactive cytotoxicity assay kit (Promega, Southampton, UK) as directed by the manufacturer's instructions. Quantification of BrdU incorporation into the cells was determined using the cell proliferation biotrack ELISA system (GE Healthcare, Chalfont St Giles, UK) as per the manufacturer's instructions. Differences were analysed using paired t-tests (GraphPad Prism 5, California, USA).

NF-κB Assays

NF-κB is activated downstream of TLR signalling in epithelial cells and plays a key role in regulating the immune response to infection, particular inducing a pro-inflammatory response. In order to determine the effect of pathogen and probiotic on this pro-inflammatory signal, NF-κB activity was measured by luciferase assays. Caco-2 cells (colonic human adenocarcinoma cells) were seeded into 12-well tissue culture plates at an initial density of $6 \times 10^5$ cells per well. After 2 days of culture, cells were transfected with a reporter plasmid having an NF-κB response element, pGL4.32 (Promega), and the internal control reporter pGL4.74 (Promega) using lipofectamine (Invitrogen, California, USA). 24 hours later, the medium was replaced with 1×HBSS (Invitrogen) and bacteria were added at an MOI of 30. After 40 hours, cells were lysed and luciferase activity was quantified using a Dual Luciferase Reporter Assay (Promega) as per the manufacturer's instructions. Differences were analysed using paired t-tests (GraphPad Prism 5). T84 cells could not be efficiently transfected using these reporter plasmids and therefore results are not shown.

Detection of IL-8

IL-8 is released by epithelial cells subsequent to NF-κB signalling and its release causes the recruitment of inflammatory cells. In order to determine the effect of potential probiotic strains on IL-8 production T84 cells were seeded into 12-well tissue culture plates at an initial density of $6 \times 10^5$ cells per well. After 3 days of culture, the medium was replaced with antibiotic-free medium and bacteria added at an MOI of 30. After 6 hours supernatants were harvested. Cytotoxicity was determined as above and production of IL-8 was quantified by ELISA using the human IL-8/CXCL8 DuoSet (R&D Systems, Minneapolis, USA) as per the manufacturer's instructions. IL-8 production was corrected for cell death and differences were analysed using paired t-tests (GraphPad Prism 5). Caco-2 cells did not produce sufficient levels of IL-8 and therefore results are not shown.

Growth of Epithelial Cell Monolayers and Challenge With Bacteria

In order to determine whether the present inventors' candidate probiotic strains could cross the epithelial barrier and whether they had any effect on the passage of pathogenic *E. coli* strains, Caco-2 and T84 cells were seeded onto 12-mm Transwell membranes (12 mm diameter, 3 µm pore size; Corning Glass Works, Corning, N.Y.) in 12-well tissue culture plates at an initial density of $3 \times 10^5$ cells per insert. Plates were incubated at 37° C. in 5% $CO_2$ for 8-10 days until the cells formed confluent monolayers and the transepithelial resistance (TEER) was greater than 300 $\Omega/cm^2$ as measured with an epithelial voltmeter as an indicator of membrane permeability. The medium was then changed to one that was antibiotic free and bacteria were added to the apical well of the Transwell insert at an MOI of 30. TEER of all monolayers was measured at 2 hour intervals up to 12 hours and bacteria in the basal well were enumerated every 2 hours up to 10 hours. Differences were evaluated at each time point using paired t-tests (GraphPad Prism 5). In a separate experiment, medium was removed from the Transwells after 10 hours and the monolayers were examined as detailed below.

Occludin Staining

Occludin is a component of almost all tight cell junctions therefore in order to determine tight junction breakdown Transwell inserts were fixed in ice-cold methanol at 4° C. overnight. Inserts were washed in PBS and the cells permeabilised with 0.1% Triton X-100 for 10 minutes before being washed again. Mouse anti-occludin monoclonal antibody (Zymed, California, USA) was diluted 1/200 and added to the apical chamber of the insert and incubated at room temperature for 45 minutes. Inserts were then washed in PBS and incubated for a further 45 minutes with TRITCconjugated isotype-specific goat anti-mouse antibody (Southern Biotech, Birmingham, Ala., USA) diluted 1/100 in the apical chamber. The inserts were then washed with PBS and the membranes were cut out of the inserts with a scalpel and mounted on slides with Vectashield containing DAPI (Vector Laboratories, California, USA). Fluorescent staining was examined on a Leica DMRA microscope equipped with a Hamamatsu Orca-ER monochrome camera. Ten fields of view per slide at 40× magnification were digitised using Leica Q-Fluoro software. Images were viewed using ImageJ software (http://rsb.info.nih.gov/ij) and positive pixels automatically counted as previously described (32). The significance of differences was determined by one-way ANOVA (GraphPad Prism 5).

T cell Isolation and Culture

Intestinal lamina propria leukocytes were isolated in order to determine the effect of pathogenic *E. coli* strains and potential probiotics on the adaptive immune response. Resected intestinal tissue was collected from patients undergoing surgery for complications associated with Crohn's disease or ulcerative colitis and from patients with colorectal cancer after informed consent and with appropriate ethical approval. The mucosa was separated from the muscle, cut into small fragments and incubated in collagenase (100 U/ml; Sigma) for 2 hours at 37° C. Cells were washed in PBS and leukocytes purified over discontinuous Percoll gradients (35-75%; GE Healthcare). The cell count and viability was determined by trypan blue exclusion. Cells were resuspended to a final concentration of $5 \times 10^6$/ml in RPMI 1640 supplemented with 10% FCS, 1 mM sodium pyruvate, 2 mM L-glutamine and 50 µg/ml gentamicin and cultured on top of a type I collagen gel (PureCol; Nutacon BV, The Netherlands). It has previously been shown that co-culture of lamina propria T cells with ECM components prevents activation-induced apoptosis (33) and, in particular, ligation of $\beta_1$ integrins (34); type I collagen is used as a supporting material in order to allow leukocytes to survive and proliferate. Bacterial cell sonicates were added to each well at an equivalent concentration to an MOI of 30 and cells were cultured for 5 days at 37° C. with 5% $CO_2$. After 5 days leukocytes were liberated from the collagen gel by the addition of collagenase (1000 U/ml). Cells were washed and counted before RNA extraction.

RT-qPCR

RT-qPCR was used to determine the relative expression of mRNA relating to Th1, Th2, Th17 and Treg responses and associated cytokines. RNA was extracted from the cultured leukocytes using a Macherey-Nagel NucleoSpin RNA II Isolation Kit (ABgene, Epsom, UK). Synthesis of cDNA was carried out using 500 ng of random hexamers using the ImProm-II Reverse Transcription System (Promega) in a final volume of 20 µl. All reactions were prepared according to the manufacturer's instructions giving a final magnesium chloride concentration of 3 mM. All cDNAs were diluted to a final volume of 100 µl (1/5 dilution) using EB buffer (10 mM Tris HCl pH 8.4; Qiagen Ltd., Crawley, UK). Primers and probes were designed using Primer 3 (http://frodo.wi.mit.edu/primer3) and M-Fold using the human specific GenBank sequences for T-box21 (accession number NM_013351), GATA-3 (accession number NM_001002295), RORC (accession number NM_005060), Foxp3 (accession number NM_017009), IFNγ (accession number NM_000619), TNFα (accession number NM_000594), IL-4 (accession number NM_000589), IL-462 (accession number NM_172348), IL-17A (accession number NM_002190), IL-10 (accession number NM_000572) and TGFβ (accession number NM_000660). The housekeeper gene hydroxymethylbilane synthase (HMBS) was used as an internal control. Quantitative PCR (qPCR) was performed using HotStarTaq Master Mix (Qiagen Ltd.). Gene specific amplification was performed using 0.2 µM of each primer, 0.1 µM of probe or SYBR Green 1 (1/100,000; Sigma) and 5 µl of diluted cDNA in a final volume of 25 µl. Magnesium chloride concentrations were adjusted to 4.5 mM in the final reaction by addition of 50 mM $MgCl_2$. Sample incubations were performed in an MxPro3005P (Stratagene, Calif., USA) at 95° C. for 15 minutes and then 45 cycles of 95° C. for 15 seconds, and 60° C. for 30 seconds during which the fluorescence data were collected. Data is expressed as the relative change in mRNA transcription following treatment and is normalised for cell number. No significant differences were seen between cells isolated from the three disease states and therefore results were pooled for analysis. Differences were analysed using paired t-tests (GraphPad Prism 5).

Growth of Bacteria With Noradrenaline

Noradrenaline can remove iron from chelators and supply it to bacteria. A number of LAB were cultured with and without noradrenaline to determine whether they were capable of responding to it, or the iron provided by it (Table 1). While the addition of noradrenaline had no effect on most LAB studied, two strains significantly increased their growth in response to it: *L. acidophilus* ASF360 increased its growth more than 7-fold at 48 hours and *S. thermophilus* J8010 (NCIMB 41856) increased growth at all time points studied, with a maximum of an almost 5-fold increase at 48 hours (Table 1). These two strains were chosen for further characterisation of their probiotic potential, alongside *E. coli* Nissle 1917 which has been used for the treatment of IBD (7). * indicates that growth rate for the strain is significantly greater than the average for all strains at that time point.

TABLE 1

Response of lactic acid bacteria to noradrenaline

| | 24 Hours | 48 Hours | 72 Hours |
|---|---|---|---|
| L. bulgaricus JB005 | 1.227 ± 0.215 | 1.328 ± 0.279 | 1.266 ± 0.125 |
| L. casei JB006 | 0.848 ± 0.144 | 1.191 ± 0.180 | 1.440 ± 0.017 |
| L. casei JB008 | 1.140 ± 0.074 | 1.035 ± 0.125 | 1.357 ± 0.446 |
| L. acidophilus ASF360 | 1.285 ± 0.179 | 7.725 ± 2.519 * | 2.375 ± 0.937 |
| L. salivarius ASF361 | 1.021 ± 0.128 | 0.865 ± 0.175 | 1.187 ± 0.173 |
| L. plantarum JB012 | 1.014 ± 0.170 | 0.943 ± 0.115 | 1.112 ± 0.250 |
| L. helveticus JB011 | 0.999 ± 0.114 | 1.003 ± 0.097 | 1.004 ± 0.214 |
| B. animalis JB007 | 0.998 ± 0.313 | 1.246 ± 0.398 | 1.037 ± 0.326 |
| B. bifidum JB009 | 1.175 ± 0.134 | 1.209 ± 0.172 | 1.190 ± 0.169 |
| S. thermophilus JB004 | 0.986 ± 0.296 | 1.374 ± 0.109 | 1.576 ± 0.439 |
| S. thermophilus NCIMB 41856 | 1.700 ± 0.242 * | 4.798 ± 0.868 * | 3.869 ± 1.954 * |

Proliferation and Death of Epithelial Cells

Figure 1:
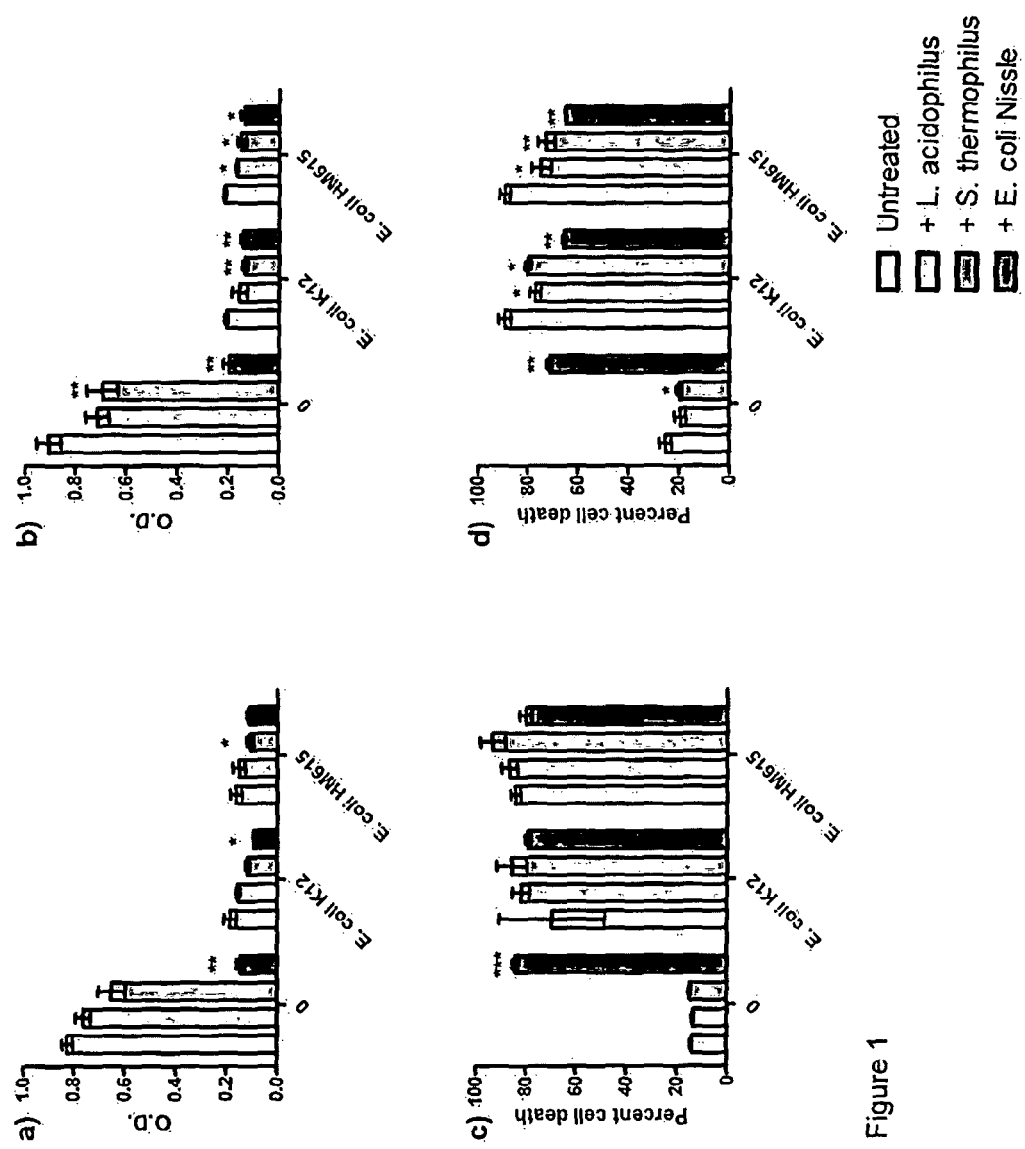

T84 and Caco-2 adenocarcinoma cells were incubated with the potential probiotics *L. acidophilus* ASF360, *S. thermophilus* J8010 (NCIMB 41856) and *E. coli* Nissle 1917 to determine their effect on the proliferative or apoptotic cellular response to pathogenic *E. coli* strains, K12 and the Crohn's disease-associated AIEC strain HM615 (35). All *E. coli* strains, including *E. coli* Nissle 1917, reduced the proliferation of T84 epithelial cells: *E. coli* K12 reduced proliferation by 78% compared to untreated cells (p=0.002); AIEC HM615 reduced proliferation by 80% (p=0.0001); and *E. coli* Nissle 1917 by 82% (p=0.001) (FIG. 1A). A similar reduction in proliferation of Caco-2 cells was seen following *E. coli* treatment: *E. coli* K12 induced a reduction of 77% compared to untreated cells (p=0.003); AIEC HM615 induced a reduction by 76% (p=0.003); and *E. coli* Nissle 1917 by 78%, (p=0.004) (FIG. 1C). Simultaneously, cell death was increased in both T84 and Caco-2 cells; *E. coli* K12 induced a 254% increase in cell death in Caco-2 cells (p=0.0005); AIEC HM615 induced a 498% increase in death in T84 cells (p=0.0003) and a 254% increase in Caco-2 cell death (p=0.001); *E. coli* Nissle 1917 induced a 498% increase in T84 cell death (p<0.0001) and a 218% increase in Caco-2 cell death (p=0.001) (FIG. 1D). *S. thermophilus* JB010 (NCIMB 41856) reduced the proliferation of Caco-2 cells treated with *E. coli* K12 or AIEC HM615 by 35% (p=0.003) and 31% (p=0.05), respectively; while *E. coli* Nissle 1917 reduced proliferation induced by *E. coli* K12 by 32% (p=0.007) and 37% in response to AIEC HM615 treatment (p=0.03) (FIG. 1B). In addition, *L. acidophilus* ASF360 further reduced proliferation of Caco-2 cells treated with AIEC HM615 by 22% (p=0.02) (FIG. 1B). *S. thermophilus* JB010 (NCIMB 41856) reduced proliferation of T84 cells treated with AIEC HM615 and *E. coli* Nissle 1917 by 33% (p=0.03) and 48% (p=0.03), respectively (FIG. 1A). Importantly, all three probiotic strains reduced death of Caco-2 cells following challenge with both *E. coli* K12 and HM615: *L. acidophilus* ASF360 reduced death of epithelial cells by 14% (p=0.04) following *E. coli* K12 treatment and 16% following infection with AIEC HM615 (p=0.03); *S. thermophilus* J8010 (NCIMB 41856) reduced death of epithelial cells following *E. coli* K12 and AIEC HM615 treatment by 10% (p=0.01) and 18 (p=0.007), respectively; *E. coli* Nissle 1917 reduced death of epithelial cells following *E. coli* K12 and treatment by 26% (p=0.006) and 27% (p=0.003), respectively (FIG. 1D). In addition, *S. thermophilus* JB010 (NCIMB 41856) was able to reduce proliferation and cell death of untreated Caco-2 cells by 24% (p=0.008) and 22% (p=0.02) respectively (FIGS. 1B and D).

Induction of NF-κB and IL-8

Figure 4:
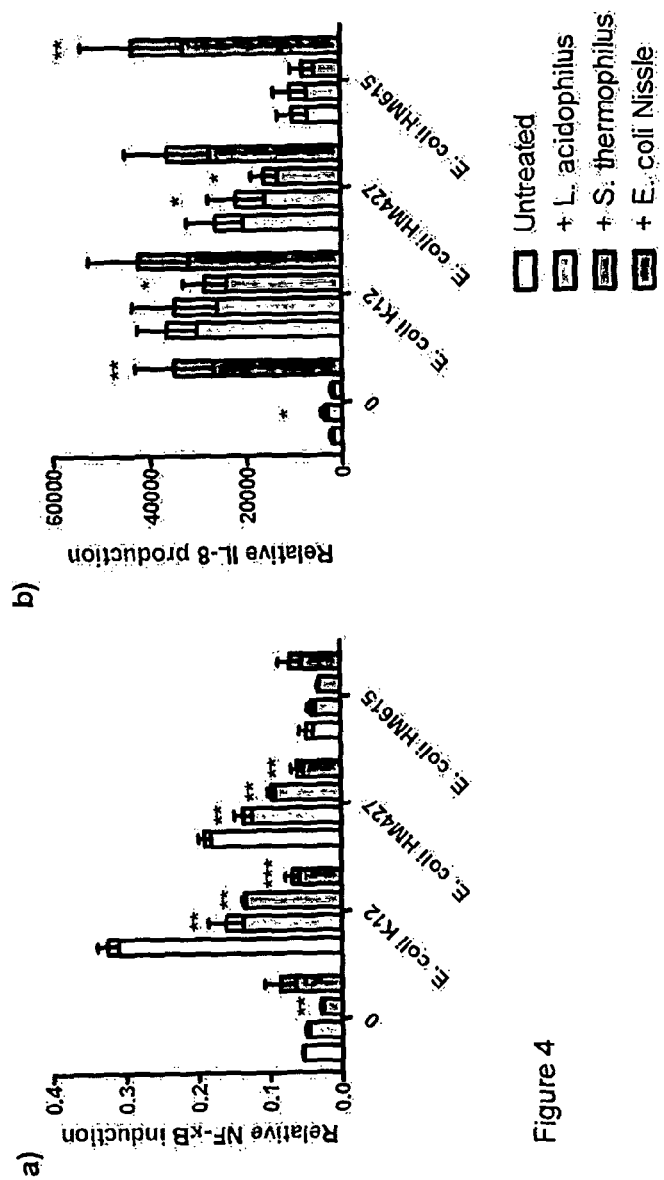

Monolayers of Caco-2 and T84 cells were treated with the three potential probiotic bacterial strains in combination with pathogenic *E. coli* strains in order to determine the effect of probiotic on either of these pro-inflammatory signalling events. NF-κB signalling in Caco-2 cells was upregulated by 491% (p=0.002) compared to controls following infection with *E. coli* K12 and by 247% (p=0.002) following AIEC HM427 treatment. However, this induction was reduced by the addition of all three probiotic strains: *L. acidophilus* ASF360 reduced the NF-κB response to *E. coli* K12 by 50% (p=0.006) and AIEC HM427 by 28% (p=0.007); *S. thermophilus* J8010 (NCIMB 41856) reduced the NF-κB response to *E. coli* K12 by 58% (p=0.002) and AIEC HM427 by 49% (p=0.005); and *E. coli* Nissle 1917 reduced the NF-κB response to *E. coli* K12 by 79% (p=0.0005) and AIEC HM427 by 68% (p=0.004) (FIG. 4A). 41856) also reduced NF-κB signalling by 48% in untreated cells (p=0.003) (FIG. 4A). Following NF-κB signalling, IL-8 production was increased by 1566% in response to *E. coli* K12 (p=0.001), 1104% in response to AIEC HM427 (p=0.004) and 363% in response to HM615 (p=0.02), as well as a 1498% increase following addition of *E. coli* Nissle 1917 (p=0.004). The IL-8 response to *E. coli* K12 was reduced by 22% following addition of *S. thermophilus* J8010 (NCIMB 41856) (p=0.02) and the response to AIEC HM427 was reduced by both *L. acidophilus* ASF360 and *S. thermophilus* J8010 (NCIMB 41856) by 17% (p=0.02) and 39% (p=0.02) respectively (FIG. 4B).

Maintenance of Epithelial Barrier Integrity

Figure 6:
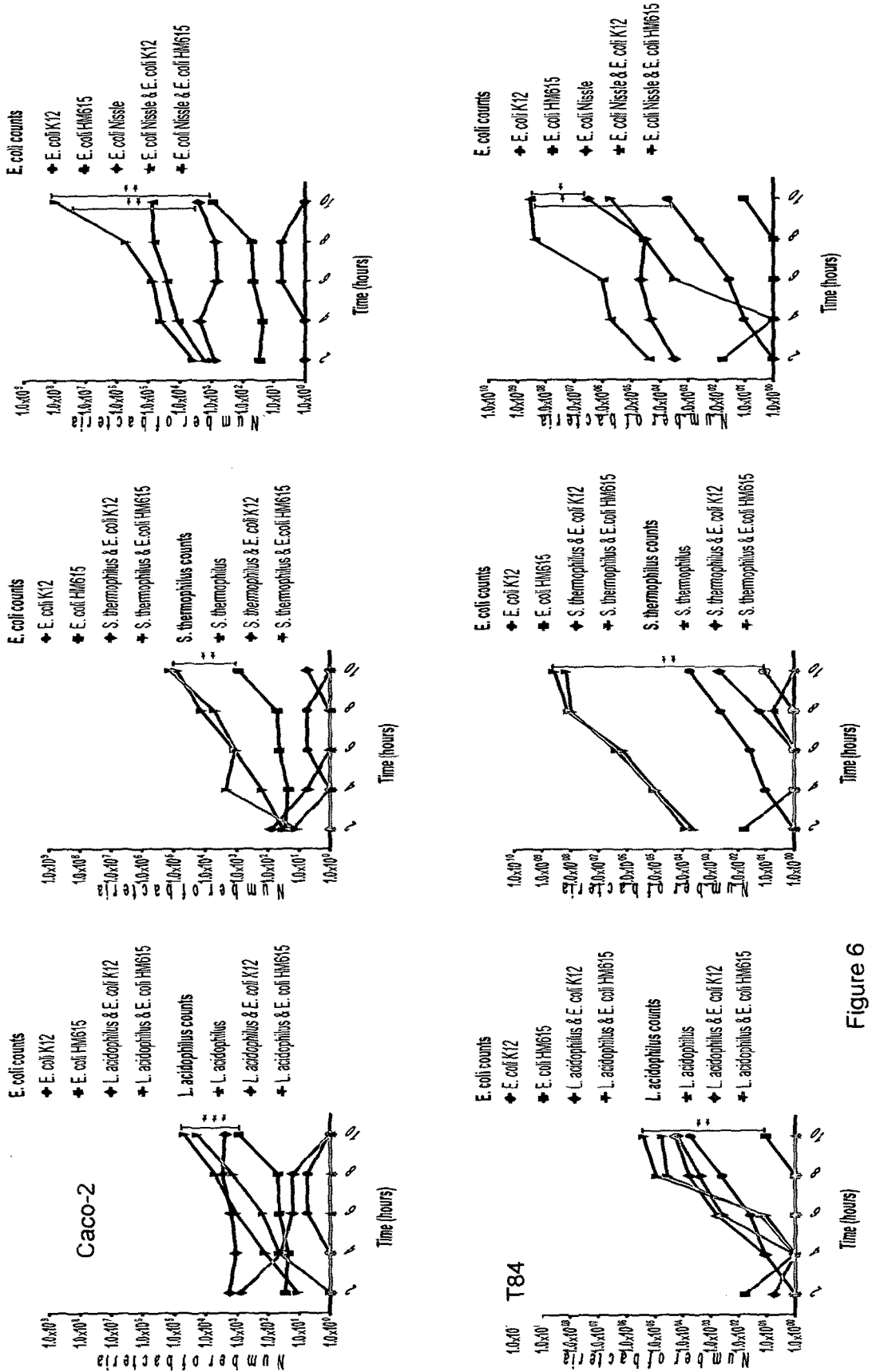

To determine the effect of our probiotic strains on epithelial barrier integrity, Caco-2 and T84 cells were grown in a Transwell system and challenged with *E. coli* K12 or AIEC HM615 in combination with each of the potential probiotics; TEER and bacterial translocation were measured. Both Caco-2 and T84 cells formed stable monolayers after 8-10 days. Neither *L. acidophilus* ASF360 nor *S. thermophilus* J8010 (NCIMB 41856) had any effect on TEER alone. However, *S. thermophilus* J8010 (NCIMB 41856) blocked the passage of *E. coli* K12 through the monolayer, a phenomenon not seen with *L. acidophilus* ASF360 which enhanced the passage of *E. coli* K12 across the barrier (FIG. 6). In addition, *S. thermophilus* J8010 (NCIMB 41856) reduced the response to *E. coli* K12, by increasing TEER, in a way that *L. acidophilus* ASF360 did not; when *S. thermophilus* J8010 (NCIMB 41856) and *E. coli* K12 were added to the monolayer simultaneously, an increase in TEER was seen (peaking at 33% in Caco-2 cells at 6 hours and 30% in T84 cells at 10 hours compared to K12 stimulated cells), whereas *L. acidophilus* ASF360 and *E. coli* K12 together caused a decrease in TEER (peaking at 56% in Caco-2 cells at 8 hours and 11% in T84 cells at 6 hours compared to K12 stimulated cells) (FIGS. 2 and 3). While AIEC HM615 alone slowly migrated through the monolayer, both *L. acidophilus* ASF360 and *S. thermophilus* J8010 (NCIMB 41856) appeared to interact with this strain and facilitate its migration across the epithelial monolayer. In this situation, translocation of *L. acidophilus* ASF360 and *S. thermophilus* J8010 (NCIMB 41856) was increased until these probiotic strains were present in equal numbers to the pathogenic strain (FIG. 6). The potentially probiotic *E. coli* strain Nissle 1917, similarly to *L. acidophilus* ASF360 and *S. thermophilus* J8010 (NCIMB 41856), had no effect on TEER (FIGS. 2 and 3) but it was able to translocate quickly without the need to interact with pathogenic *E. coli* strains (FIG. 6).

Maintenance of Tight Cell Junctions

Figure 7:
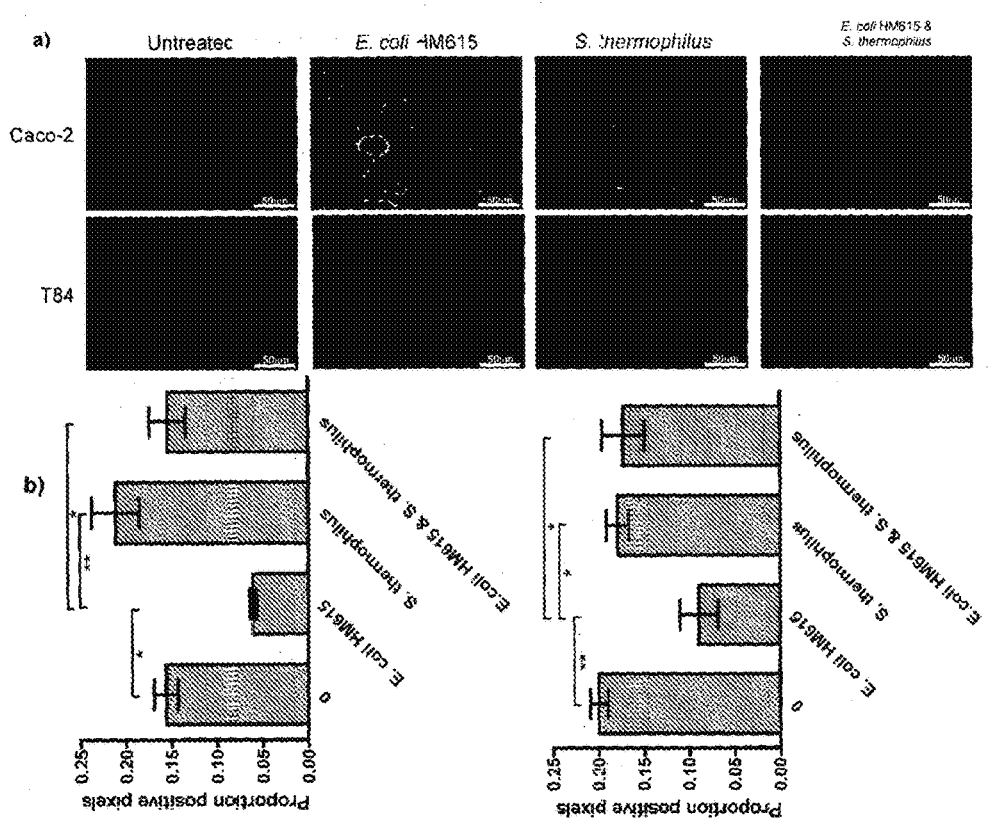
FIG. 7 is a series of photographs showing the expression of occludin (red in colour originals; light grey in black and white) in epithelial cell monolayers (a). b) Proportion of pixels positive for occludin staining relative to entire field of view. Results are expressed as mean±S.E.M. * $p \leq 0.05$ and ** $p \leq 0.01$.

Caco-2 and T84 cells were grown in a Transwell system and infected with AIEC HM615; *S. thermophilus* J8010 (NCIMB 41856) was added to determine its effect on the tight cell junction protein occludin. AIEC HM615 caused the breakdown of tight cell junctions in Caco-2 and T84 monolayers, illustrated by decreased occludin (61% and 56% respectively) (FIG. 7). AIEC HM615 also caused a 24% decrease in nuclear staining of T84 cells (data not shown), indicating that it was inducing cell death. The addition of *S. thermophilus* J8010 (NCIMB 41856) to the monolayers in conjunction with AIEC HM615 prevented AIEC-induced tight cell junction breakdown and cell death; levels of nuclear and occludin staining were unchanged from control monolayers (FIG. 7).

Skewing of Effector T Cell Responses

Figure 8:
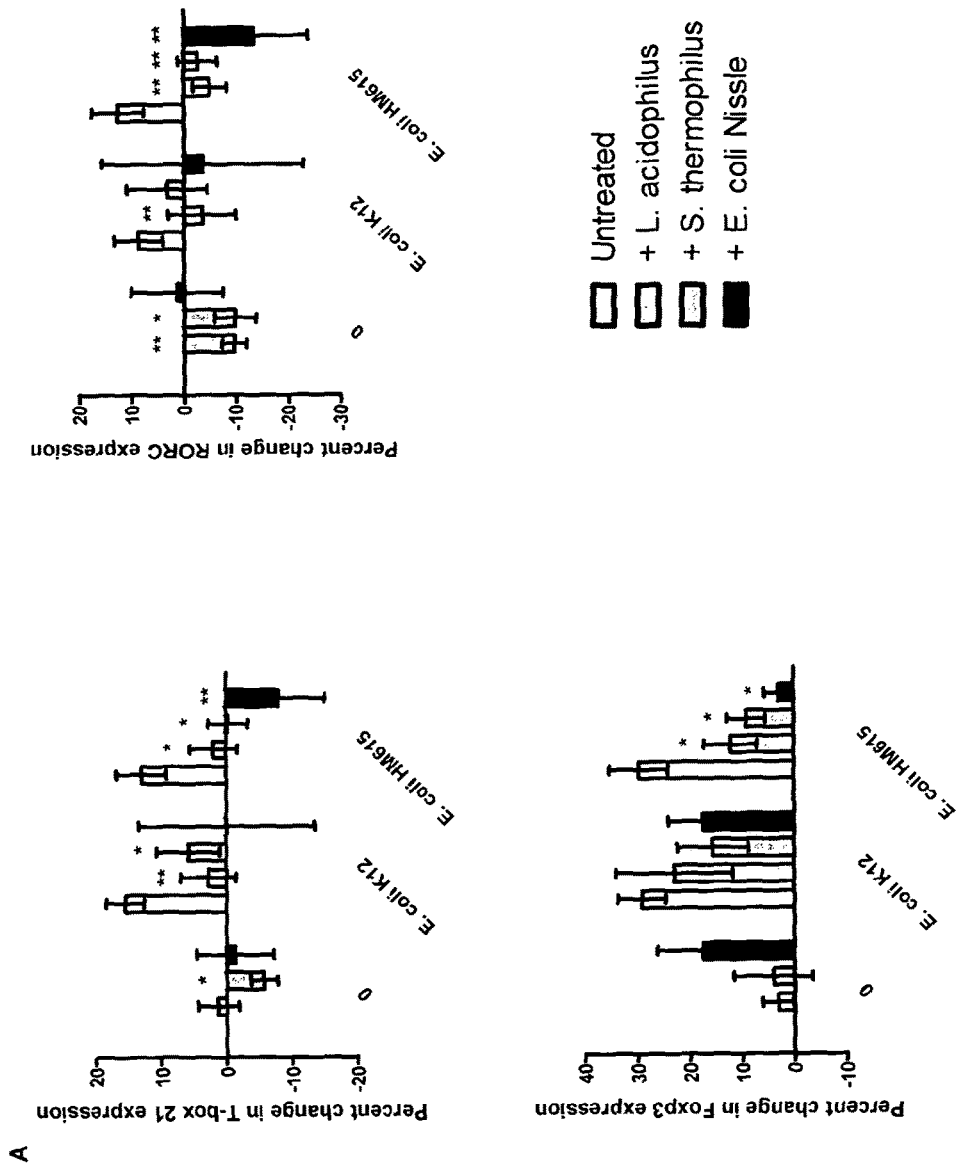
FIG. 8 is a series of graphs illustrating the percent change in expression of T-box21 (Th1), RORC (Th17) and Foxp3 (Treg) transcription factor mRNA in response to *E. coli* and the effect of probiotics on their expression. Results are expressed as mean±S.E.M. * $p \leq 0.05$ and ** $p \leq 0.01$.
Figure 12:
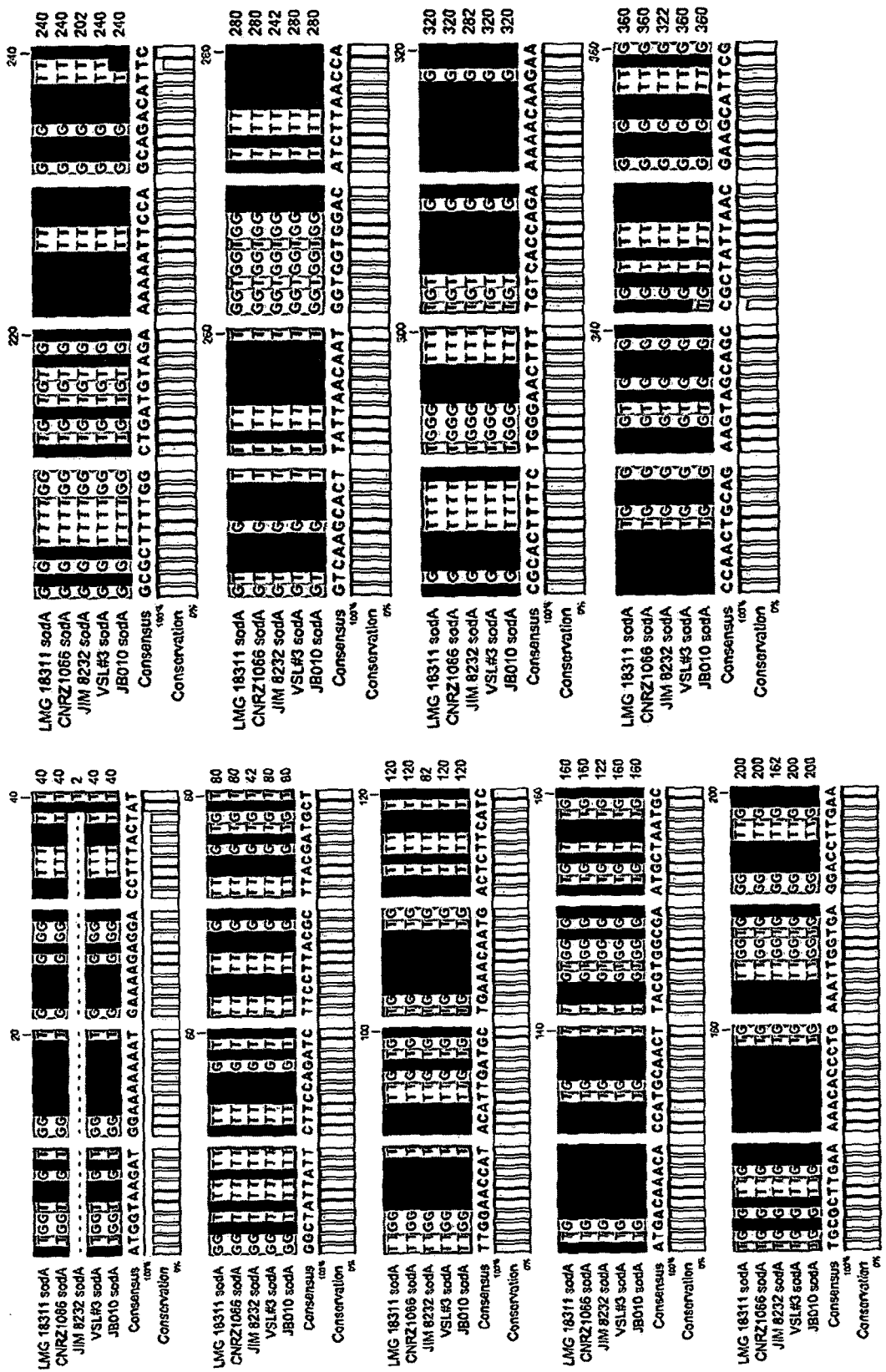
FIG. 12 shows the comparative alignment of the sodA gene of the lactic acid bacterial strains LMG 18311, CNRZ1066, JIM 8232, VSL#3, and JMB010 (*Streptococcus thermophilus* NCIMB 41856)
Figure 13:
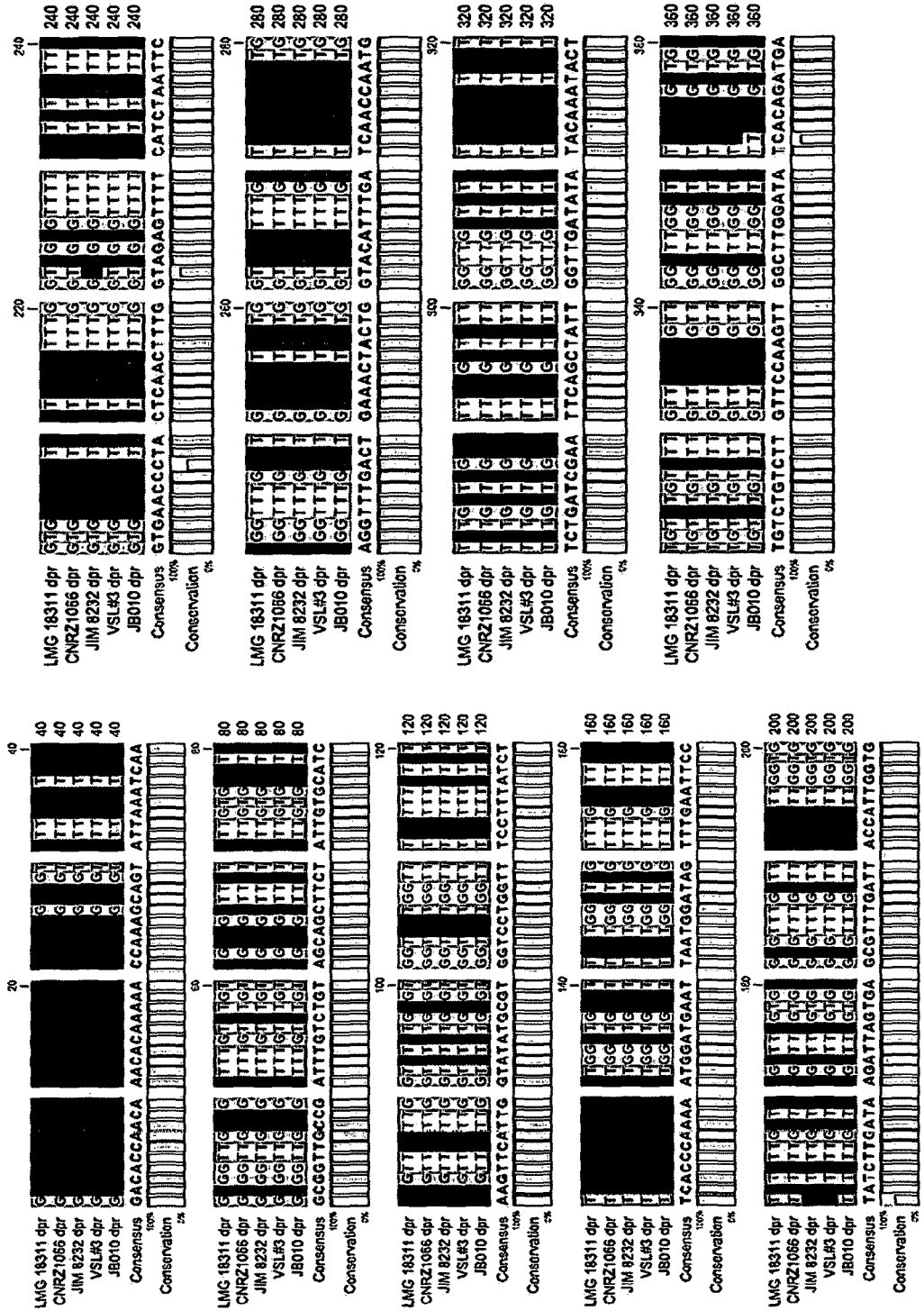
FIG. 13 shows the comparative alignment of the dpr gene of the lactic acid bacterial strains LMG 18311, CNRZ1066, JIM 8232, VSL#3, and JMB010 (*Streptococcus thermophilus* NCIMB 41856)
Figure 14:
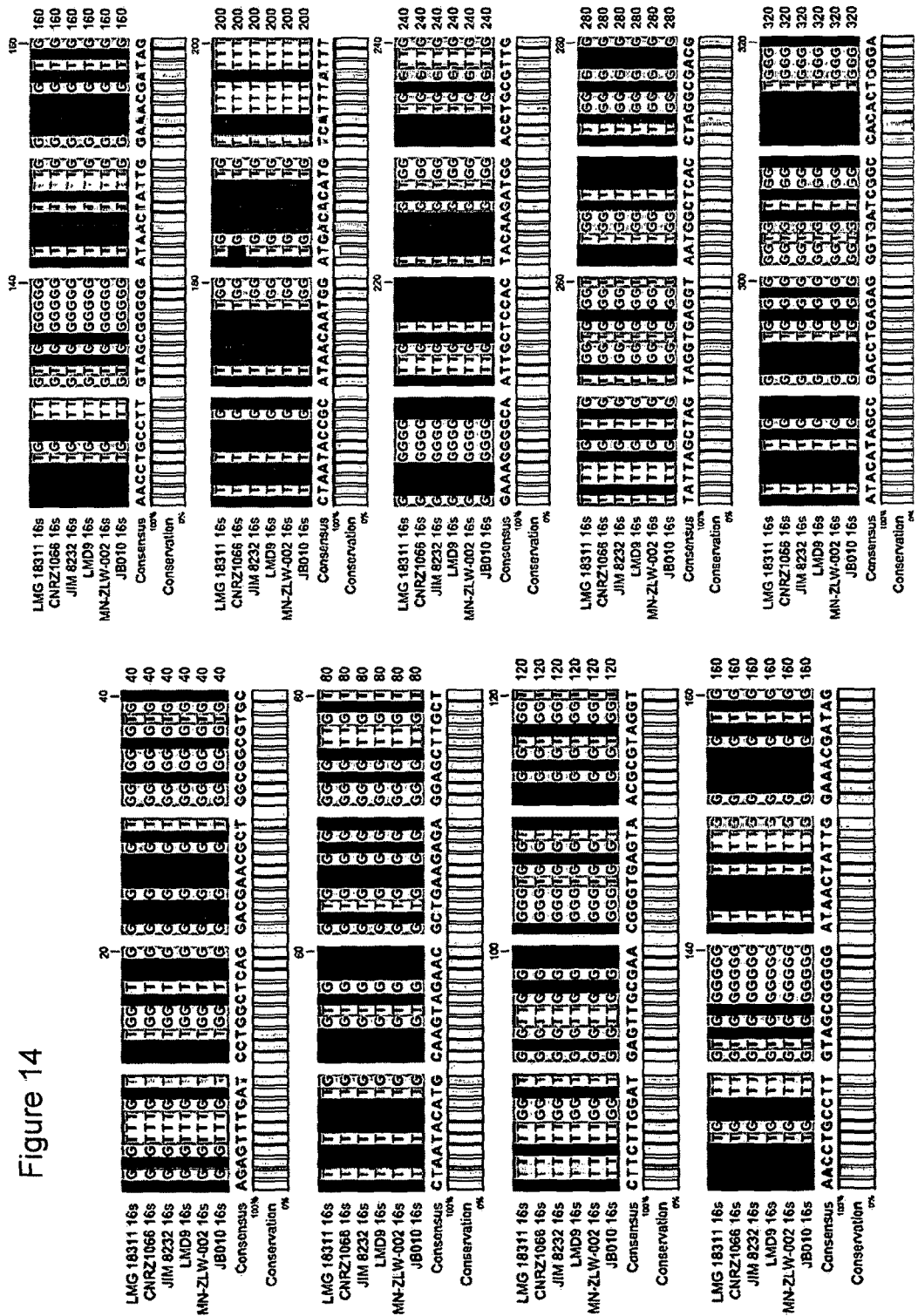
FIG. 14 shows the comparative alignment of the 16S gene of the lactic acid bacterial strains LMG 18311, CNRZ1066, JIM 8232, VSL#3, and JMB010 (*Streptococcus thermophilus* NCIMB 41856)
Figure 15:
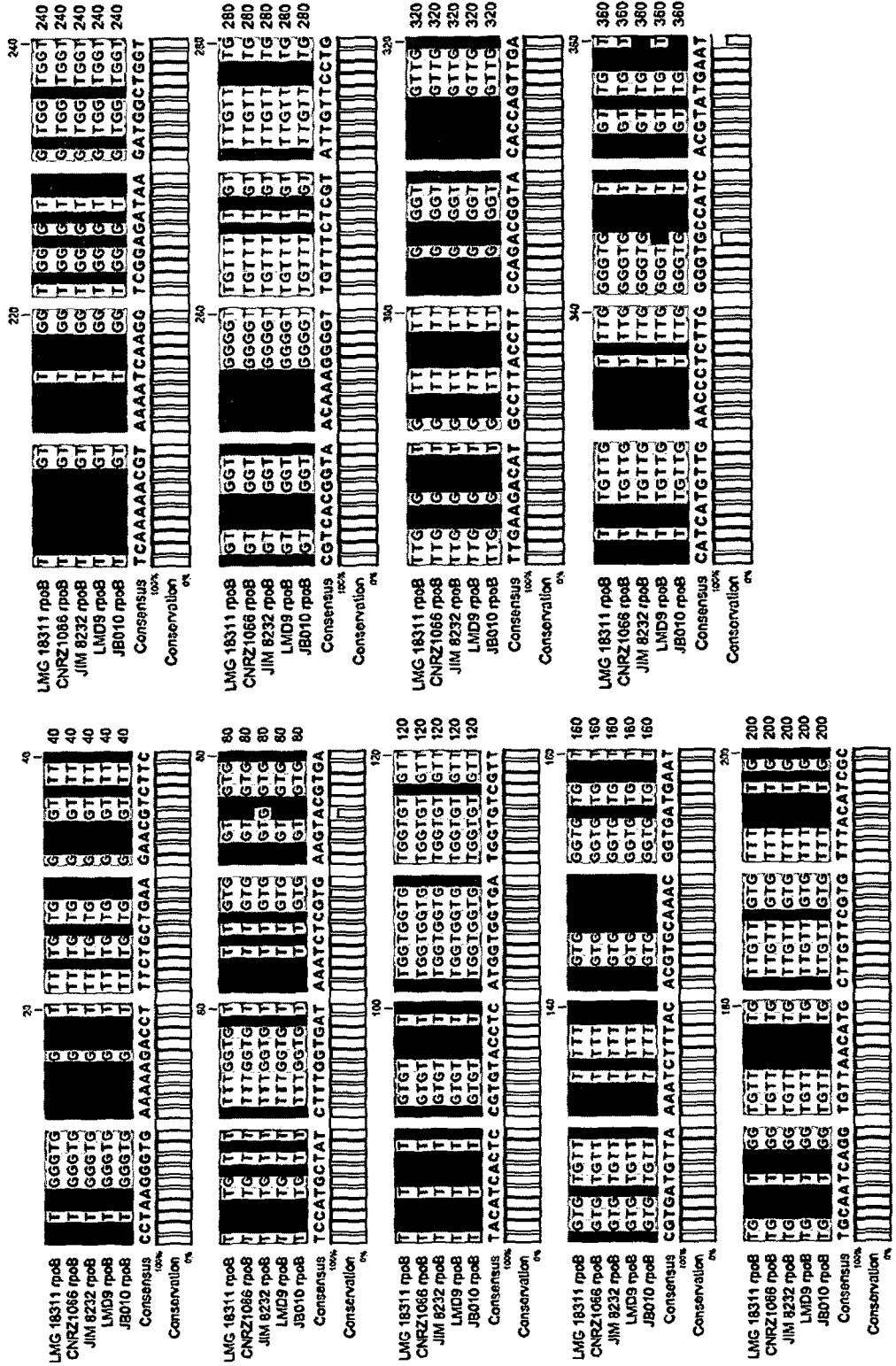
FIG. 15 shows the comparative alignment of the rpoB gene of the lactic acid bacterial strains LMG 18311, CNRZ1066, JIM 8232, VSL#3, and JMB010 (*Streptococcus thermophilus* NCIMB 41856)

Leukocytes were isolated from the intestinal lamina propria and challenged with bacterial antigens from *E. coli* K12 and AIEC HM615 to determine the effect of competing probiotic antigens from *L. acidophilus* ASF360, *S. thermophilus* J8010 (NCIMB 41856) and *E. coli* Nissle 1917. Both *E. coli* K12 and AIEC HM615 induced a Th1 response, indicated by upregulation of mRNA encoding the Th1-specific transcription factor T-box21 in the population of cultured leukocytes (16% (p=0.003) and 13% (p=0.007) respectively); this was significantly reduced by the addition of *L. acidophilus* ASF360 or *S. thermophilus* J8010 (NCIMB 41856). *L. acidophilus* ASF360 reduced the response to *E. coli* K12 and AIEC HM615 by 13% (p=0.003) and 11% (p=0.02), respectively. *S. thermophilus* J8010 (NCIMB 41856) reduced the Th1 response to *E. coli* K12 and AIEC HM615 by 10% (p=0.03) and 13% (p=0.04), respectively. *E. coli* Nissle 1917 also downregulated the Th1 response to AIEC HM615 by 21% (p=0.009). Furthermore, *S. thermophilus* J8010 (NCIMB 41856) reduced the baseline level of transcription of T-box21 in untreated cells by 6% (p=0.03). Neither *E. coli* strain induced a significant Th2 response but the Th17-specific transcription factor, RORC, was also upregulated following treatment with *E. coli* K12 or AIEC HM615 antigens (9% and 13% (p=0.02), respectively). The Th17 response to *E. coli* K12 was reduced by 12% following the addition of *L. acidophilus* ASF360 antigens (p=0.009) and the response to AIEC HM615 was reduced by the addition of any of the three potential probiotic strains: *L. acidophilus* ASF360 reduced the response by 18% (p=0.0002), *S. thermophilus* J8010 (NCIMB 41856) by 15% (p=0.003) and *E. coli* Nissle 1917 by 26% (p=0.003). In addition, both *L. acidophilus* ASF360 and *S. thermophilus* J8010 (NCIMB 41856) were capable of reducing the baseline level of RORC transcription in untreated cells by 10% (p=0.003 and p=0.04, respectively). AIEC HM615 also induced a strong Treg response, shown by the upregulation of Foxp3 by 30% (p=0.0009) in cultured leukocytes. However, this was reduced by the addition of any of the three potential probiotic strains: *L. acidophilus* ASF360 caused an 18% reduction in Foxp3 expression (p=0.02), *S. thermophilus* J8010 (NCIMB 41856) a 21% reduction (p=0.03) and *E. coli* Nissle 1917 a 27% reduction (p=0.02) (FIG. 8).

T Cell Cytokine Production

Figure 5:
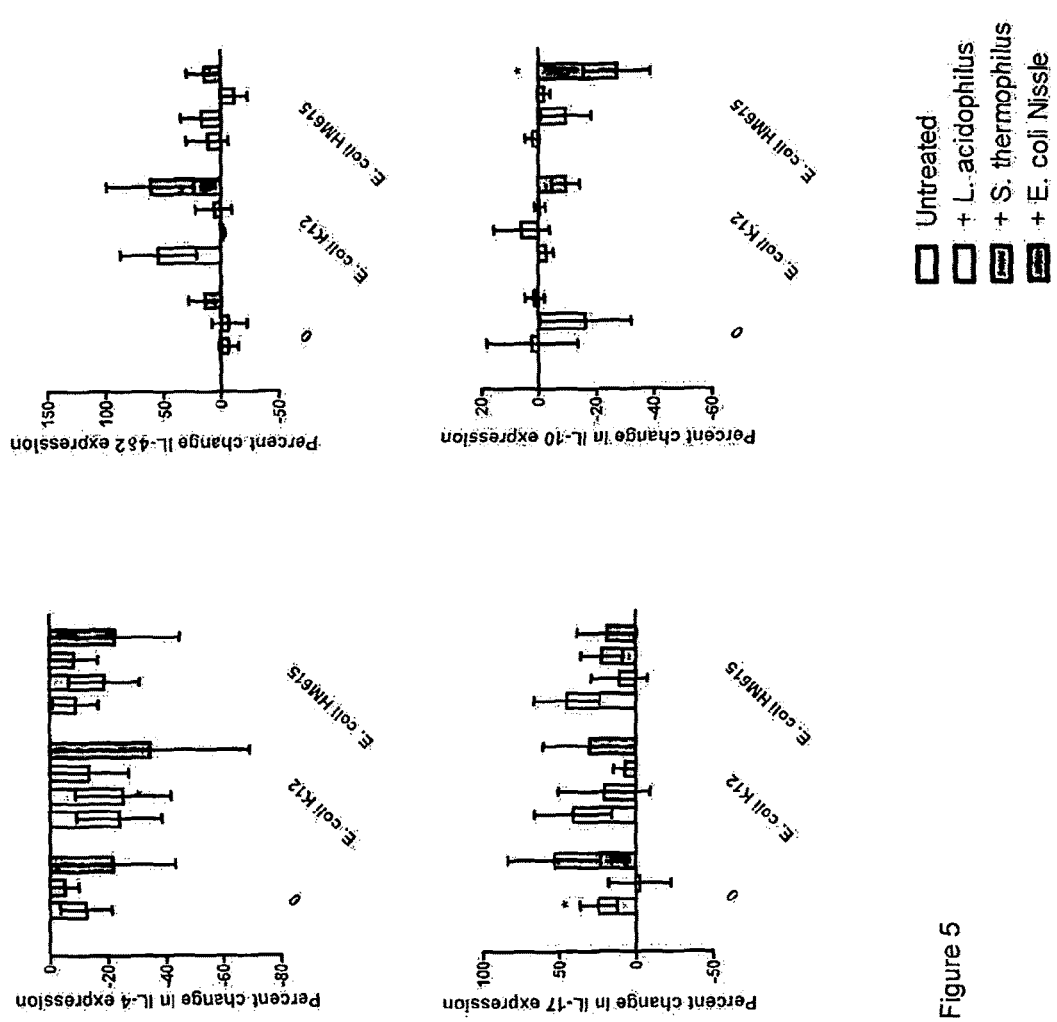

In accordance with the transcription factor data previously described, both *E. coli* K12 and AIEC HM615 induced upregulation of TNFα mRNA in cultured leukocyte populations (9% and 12% respectively), indicating a Th1 response. Despite this, neither *E. coli* K12 or AIEC HM615 induced a significant IFNγ response, although IFNγ mRNA production was increased by 15% when *E. coli* K12 and Nissle 1917 were used in combination (p=0.04) and decreased by 16% following treatment with *L. acidophilus* ASF360 (p=0.01) or by 10% following treatment with *S. thermophilus* J8010 (NCIMB 41856) (p=0.02) alone. The TNFα response to *E. coli* K12 was reduced by 16% by the addition of *L. acidophilus* ASF360 (p=0.03) whereas *S. thermophilus* J8010 (NCIMB 41856) reduced the level of TNFα mRNA produced in response to AIEC HM615 by 20% (p=0.03) (FIG. 9). As expected, there was no significant change in the production of the Th2-related cytokine IL-4. Although not significant, both *E. coli* strains appeared to increase the expression of IL-462 mRNA, the naturally occurring antagonist of IL-4, further indicating skewing towards a Th1 response. However, evidence for a Th17 response was seen in the increased expression of IL-17 mRNA by 45% (p=0.04) following treatment with antigens derived from AIEC HM615; this appeared to be reduced by the addition of any of the three probiotic strains, although this was not statistically significant. No significant changes were seen in the expression of IL-10 mRNA, although *E. coli* Nissle 1917 did reduce IL-10 expression by 29% when cultured in combination with AIEC HM615; however HM615 did not induce the expression of IL-10 (FIG. 5). The transcription of TGFβ was significantly increased by lamina propria leukocytes by 14% in response to *E. coli* K12 (p=0.01) and by 11% in response to AIEC HM615 (p=0.009) treatment. *L. acidophilus* ASF360 and *S. thermophilus* J8010 (NCIMB 41856) were able to reduce the induction of TGFβ mRNA by *E. coli* K12 by 12% (p=0.01) and 9% (p=0.006) to levels comparable to that of control cells. Similarly, *L. acidophilus* ASF360 and *S. thermophilus* JB010 (NCIMB 41856) also reduced the TGFβ response to AIEC HM615 by 12% (p=0.04) and 10% (p=0.009) respectively. *E. coli* Nissle 1917 was also able to reduce the expression of TGFβ mRNA induced by AIEC HM615 by 23% (p=0.01) (FIG. 9).

Adherence to Cells

Probiotic organisms are generally considered to have good adherence to intestinal cells in the same manner as commensal gut organisms and possibly even to mimic the adherence of invasive strains of enteric bacteria. In this respect, the present inventors tested the adherence of *S. thermophilus* J8010 (NCIMB 41856), *S. thermophilus* JB021, *E. coli* K12, *E. coli* HM427, and *E. coli* HM615 to Caco-2 cells.

Caco-2 human adenocarcinoma cells were grown in DMEM supplemented with 10% FCS, 2 mM L-glutamine and 100 U/ml penicillin/streptomycin in 12-well tissue culture plates at an initial density of $3 \times 10^5$ cells/well. After 3 days of culture, the medium was replaced with antibiotic-free DMEM and *S. thermophilus* or *E. coli* strains were added at an MOI of 30. Plates were set up in duplicate (each containing 3 replicate wells/treatment) and after 4 hours of incubation at 37° C. with 5% $CO_2$ one set of cells were lysed with PBS containing 1% Triton X-100 and the number of live bacteria counted using the Miles and Misra method to give total number of bacteria. To give numbers of bacteria which had invaded the epithelial cells, the second set of cells was treated with PBS containing 100 □g/ml gentamicin for 2 hours at room temperature before being lysed and the bacteria being counted. The number of adherent bacteria was calculated by subtracting the number of invasive bacteria from the total number of bacteria. The results are shown in FIG. 18. From the results it can be seen that the adherent invasive strains of *E. coli* such as *E. coli* HM427 and *E. coli* HM615 showed a significantly higher level of adherence than either of the *S. thermophilus* strains and that, surprisingly, the *S. thermophilus* J8010 (NCIMB 41856) showed the worst adherence of all of the strains tested showing that it would not normally be considered to be a useful probiotic strain.

REFERENCES

1. E. Metchnikoff, P. C. Mitchell, *The prolongation of life; optimistic studies*. (W. Heinemann; G. P. Putnam's Sons, London, New York, 1907).
2. Report of a joint FAO/WHO Expert Consultation on Evaluation of Health and Nutritional Properties of Probiotics in Food Including Powder Milk with Live Lactic Acid Bacteria (October 2001).
3. H. Szajewska, A. Skorka, M. Ruszczynski, D. Gieruszczak-Bialek, *Aliment Pharmacol Ther* 25, 871 (Apr. 15, 2007).
4. L. V. McFarland, *Travel Med Infect Dis* 5, 97 (March, 2007).
5. M. Hickson et al., *BMJ* 335, 80 (Jul. 14, 2007).
6. D. Haller et al., *J Nutr* 140, 690S (March, 2010).
7. B. J. Rembacken, A. M. Snelling, P. M. Hawkey, D. M. Chalmers, A. T. Axon, *Lancet* 354, 635 (Aug. 21, 1999).
8. A. Venturi et al., *Aliment Pharmacol Ther* 13, 1103 (August, 1999).
9. A. Tursi et al., *Med Sci Monit* 10, PI126 (November, 2004).
10. R. Bibiloni et al., *Am J Gastroenterol* 100, 1539 (July, 2005).

11. G. Pineton de Chambrun, J. F. Colombel, D. Poulain, A. Darfeuille-Michaud, *CURR. OPIN. GASTROENTEROL.* 24, 440 (July, 2008).
12. A. Pandey, F. Bringel, J. M. Meyer, *Appl Microbiol Biot* 40, 735 (January, 1994).
13. B. Bruyneel, M. Vandewoestyne, W. Verstraete, *Biotechnol Lett* 11, 401 (June, 1989).
14. M. Imbert, R. Blondeau, *Curr Microbiol* 37, 64 (July, 1998).
15. F. Archibald, *Crit Rev Microbiol* 13, 63 (1986).
16. K. G. Wooldridge, P. H. Williams, *FEMS Microbiol Rev* 12, 325 (November, 1993).
17. P. P. Freestone, R. D. Haigh, P. H. Williams, M. Lyte, *FEMS Microbiol Lett* 172, 53 (Mar. 1, 1999).
18. S. M. Sandrini et al., *J Bacteriol* 192, 587 (January, 2010).
19. M. Hoffmann et al., *J Nutr* 138, 1684 (September, 2008).
20. P. van Baarlen et al., *Proceedings of the National Academy of Sciences of the United States of America* 106, 2371 (Feb. 17, 2009).
21. U. P. Singh, C. Venkataraman, R. Singh, J. W. Lillard, Jr., *Endocr Metab Immune Disord Drug Targets* 7, 111 (Jun, 2007).
22. H. Sokol et al., *Proceedings of the National Academy of Sciences of the United States of America* 105, 16731 (Oct. 28, 2008).
23. M. Roselli et al., *Inflamm Bowel Dis* 15, 1526 (October, 2009).
24. H. K. Kwon et al., *Proceedings of the National Academy of Sciences of the United States of America* 107, 2159 (Feb. 2, 2010).
25. P. P. Freestone et al., *Shock* 18, 465 (November, 2002).
26. M. Hafez, K. Hayes, M. Goldrick, R. K. Grencis, I. S. Roberts, *Infect Immun* 78, 2153 (May, 2010).
27. C. Pagnini et al., *Proc Natl Acad Sci USA* 107, 454 (Jan. 5, 2010).
28. K. Gronbach et al., *Infect Immun* 78, 3036 (July, 2010).
29. K. C. Anukam, E. O. Osazuwa, H. B. Osadolor, A. W. Bruce, G. Reid, *Journal of Clinical Gastroenterology* 42, 239 (March, 2008).
30. J. P. Furet, P. Quenee, P. Tailliez, *Int J Food Microbiol* 97, 197 (Dec. 15, 2004).
31. C. Rodriguez, M. Medici, F. Mozzi, G. Font de Valdez, *World J Gastroenterol* 16, 1622 (Apr. 7, 2010).
32. C. F. Inman et al., *J Immunol Methods* 302, 156 (July, 2005).
33. A. Sturm, K. A. Krivacic, C. Fiocchi, A. D. Levine, *J Immunol* 173, 3889 (Sep. 15, 2004).
34. A. Stallmach et al., *Eur J Immunol* 31, 1228 (April, 2001).
35. S. Subramanian et al., *Inflamm Bowel Dis* 14, 162 (February, 2008).
36. S. G. Botina, O. V. Piksasova, Yu. D. Tsygankov, and V. V. Sukhodolets, *Russian Journal of Genetics* 43, 485 (2007).
37. E. Simova et al *J. Ind. Microbiol. Biotechnol.* 35 (2008) pp 1109-1115.
38. S. Sieuwerts et al *Appl. Env. Microbiol.* 76 (2010) 7775-7784.
39. L. Herve-Jimenez et al *Appl. Env. Microbiol.* 75 (2009) 2062-2073.

---

The invention claimed is:

1. A composition comprising a probiotic ingredient comprising:
   *Streptococcus thermophilus* deposited under accession number NCIMB 41856, and further comprising a DNA sequence according to SEQ ID NO:1 or SEQ ID NO:2; and wherein the composition is provided in the form of an enteric-coated capsule or tablet.

2. The composition according to claim 1, further comprising gelatin, cellulose, a starch, an excipient, a binder, a flavoring, an anti-caking agent, a preservative, or a combination thereof.

3. A method of treating an intestinal disease in a human or an animal, comprising orally administering to the human or animal a composition comprising a probiotic ingredient comprising:
   *Streptococcus thermophilus* deposited under accession number NCIMB 41856, and further comprising a DNA sequence according to SEQ ID NO:1 or SEQ ID NO:2, and wherein the composition is provided in the form of a powder, a capsule or a tablet.

4. The method according to claim 3, wherein the intestinal disease is associated with an increase in noradrenaline and/or bioavailability of iron in the intestine.

5. The method according to claim 4, wherein the increase in the bioavailability of iron is due to inflammation, intestinal bleeding, surgery, trauma and/or stress.

6. The method according to claim 3, wherein the intestinal disease is a chronic disease.

7. The method according to claim 6, wherein the chronic disease is Crohn's disease, ulcerative colitis, irritable bowel syndrome, coeliac disease, gastroenteritis or pancreatitis.

8. The method according to claim 3, wherein the intestinal disease is an acute disease.

9. The method according to claim 8, wherein the acute disease is due to an ulcer, infection, parasite infestation, protozoal infestation, *Helicobacter* infection, injury, trauma, stress, or a surgery.

10. The method according to claim 3, wherein the composition has a non-dairy formulation.

11. The method according to claim 3, wherein the intestinal disease is a pro-inflammatory intestinal disease.

* * * * *